US006169232B1

(12) United States Patent
Hey et al.

(10) Patent No.: US 6,169,232 B1
(45) Date of Patent: Jan. 2, 2001

(54) NUCLEOTIDE SEQUENCES OF GENES ENCODING SINK PROTEIN AND USES THEREOF FOR IMPROVING THE NUTRITIONAL QUALITY OF FEEDS

(75) Inventors: Timothy D. Hey, Zionsville; Ann Owens Merlo, Carmel; Terence A. Walsh, Zionsville, all of IN (US)

(73) Assignee: Dow AgroSciences LLC, Indianapolis, IN (US)

( * ) Notice: Under 35 U.S.C. 154(b), the term of this patent shall be extended for 0 days.

(21) Appl. No.: 09/097,767

(22) Filed: Jun. 16, 1998

Related U.S. Application Data

(60) Provisional application No. 60/052,552, filed on Jul. 15, 1997.

(51) Int. Cl.[7] .............................. C12N 5/04; C12N 5/10; C12P 21/06; C07K 1/00; A01H 9/00
(52) U.S. Cl. ..................... 800/320.1; 536/23.6; 435/412; 435/419; 435/69.1; 530/370; 530/350; 800/295; 800/298
(58) Field of Search .................. 536/23.6; 800/300.1, 800/260, 320.1, 295, 298; 435/412, 69.1, 419; 530/350, 370

(56) References Cited

FOREIGN PATENT DOCUMENTS

| 240911 | 11/1986 | (DE) . |
|---|---|---|
| WO 89/11789 | 12/1989 | (WO) . |
| WO 91/04270 | 4/1991 | (WO) . |
| WO 91/10725 | 7/1991 | (WO) . |
| WO 92/14822 | 9/1992 | (WO) . |
| WO 93/03160 | 2/1993 | (WO) . |
| WO 93/08682 | 5/1993 | (WO) . |
| WO 93/19190 | 9/1993 | (WO) . |
| WO 95/15392 | 6/1995 | (WO) . |

OTHER PUBLICATIONS

Marcellino et al. FEBS Letter. 1996. May 6 issue. vol. 385: 154–158.*
Spencer et al. Plant Molecular Biology. 1992. vol. 18: 201–210.*
Boase et al. In Vitro Cellular and Developmental Biology. 1998. vol. 34: 46–51.*
Marcellino L H et al. "Modified 2S albumins with improved tryptophan content are correctly expressed in transgenic tobacco plants" FEBS Letters, vol. 385, pp 154–158 (1996).
Coleman, G. D., et al. "Complementary DNA cloning of poplar bark storage protein and control of its expression by photoperiod" Plant Physiology, vol. 98, pp 687–693 (1991).
Clausen, S et al., "Seasonal changes in the concentration of the major stoeage protein and its mRNA in xylem ray cells of poplar trees", Plant Molecular Biology, vol. 17, pp 669–678 (1991).

* cited by examiner

Primary Examiner—Paula K. Hutzell
Assistant Examiner—Ousama Zaghmout
(74) Attorney, Agent, or Firm—Donald R. Stuart

(57) ABSTRACT

The invention disclosed herein provides genes and methods of creating and using said genes for expression in the seed of a plant like corn. When the genes are expressed endogenously, the result in the production of proteins that increase the nutritional value of the feed made from said seed. Also disclosed is a method of designing genes for use in production of proteins that can be expressed in a manner whereby the nutritional value of feed can be increased.

3 Claims, No Drawings

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 990 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:1:

```
ACC ATG GCT ACC AAG ATC CTC GCC CTG CTG GCC CTC CTC GCT CTG CTC      48
    Met Ala Thr Lys Ile Leu Ala Leu Leu Ala Leu Leu Ala Leu Leu
            -20                 -15                 -10

GTG AGC GCT ACC AAC GCT TTC ATC ATC CCC CAC CTT CGC CTC GGG CTG      96
Val Ser Ala Thr Asn Ala Phe Ile Ile Pro His Leu Arg Leu Gly Leu
            -5              -1  1                   5

GTC TTC ACA TCC GAC AAC AAC GAA CGC GCT CTC CAG AAT AGC GGG CTG     144
Val Phe Thr Ser Asp Asn Asn Glu Arg Ala Leu Gln Asn Ser Gly Leu
            10                  15                  20

TAC AGC CCT GAC TCC GAG GAC TCT TCC GTG GAC ATT GCC GGT CGT CGC     192
Tyr Ser Pro Asp Ser Glu Asp Ser Ser Val Asp Ile Ala Gly Arg Arg
        25                  30                  35

TGG CAC TCC GGC ACC CTT AAT GGG AGC TCC ATC GTC TAC GTG AAG ACA     240
Trp His Ser Gly Thr Leu Asn Gly Ser Ser Ile Val Tyr Val Lys Thr
    40                  45                  50                  55

GGC TCC CAC AGC GTC AAC ATG GCG ACG ACC CTG CAA ATC CTC TTG GCT     288
Gly Ser His Ser Val Asn Met Ala Thr Thr Leu Gln Ile Leu Leu Ala
                60                  65                  70

CGG TGG TCC ATT CAT GGC GTG ATC TAC TTT GGC AAT GCT GGC TCC CTG     336
Arg Trp Ser Ile His Gly Val Ile Tyr Phe Gly Asn Ala Gly Ser Leu
            75                  80                  85

GAC AAG AAG ACG ATG GTT CCT GGC GAC GTC TCT GTG CCA CAA GCA GTC     384
Asp Lys Lys Thr Met Val Pro Gly Asp Val Ser Val Pro Gln Ala Val
        90                  95                  100

GCA TTC ACT GGT GTG TGT AAC TGG AAG AAG TGG CGC TCC GAG AAG GGC     432
Ala Phe Thr Gly Val Cys Asn Trp Lys Lys Trp Arg Ser Glu Lys Gly
    105                 110                 115

AAA TTG GTG TTT GGT GAC TGG AAC TAT CCC GAG AAT GGC GAG AAC CTT     480
Lys Leu Val Phe Gly Asp Trp Asn Tyr Pro Glu Asn Gly Glu Asn Leu
120                 125                 130                 135

CTT GGT ACC GTC GAG TAC GAG AAG ATC AAG ATG TTC TCA CCG TCT GAT     528
Leu Gly Thr Val Glu Tyr Glu Lys Ile Lys Met Phe Ser Pro Ser Asp
            140                 145                 150

GCG CCA AAG GAA GTG TTC TGG CTG CCG ATC ACC AAG TCT TGG TAC AAC     576
Ala Pro Lys Glu Val Phe Trp Leu Pro Ile Thr Lys Ser Trp Tyr Asn
        155                 160                 165

GCT GCG ACC GAG GCG CTC AAG GAC ATG AAG CTC AGG AAG TGC TAC AGC     624
Ala Ala Thr Glu Ala Leu Lys Asp Met Lys Leu Arg Lys Cys Tyr Ser
    170                 175                 180

GAC GGG TGT CTG CCC GGT GAG CCG AAG GTG GTG TTC GGC TCG AAG TCC     672
Asp Gly Cys Leu Pro Gly Glu Pro Lys Val Val Phe Gly Ser Lys Ser
185                 190                 195

TCT ACC AGC GAC TGG TAC GTG AGG AAC AAA GCC TAT GGT GAC TGG CTC     720
Ser Thr Ser Asp Trp Tyr Val Arg Asn Lys Ala Tyr Gly Asp Trp Leu
200                 205                 210                 215

AAC GAC AAC TGG GAT GCC AAG ACT GCA GAT ACC ACC TCC GCT TCG GTT     768
Asn Asp Asn Trp Asp Ala Lys Thr Ala Asp Thr Thr Ser Ala Ser Val
            220                 225                 230

GCC CTC ACC AGC TTG AGC AAC GAG AAG CTC TTC GTG GTC TTC CAA GGA     816
Ala Leu Thr Ser Leu Ser Asn Glu Lys Leu Phe Val Val Phe Gln Gly
        235                 240                 245

GTC AGC AAC GTT GCT GGC GAG ACC TCG TCC AAC AGC AGG GTG TCA TAC     864
Val Ser Asn Val Ala Gly Glu Thr Ser Ser Asn Ser Arg Val Ser Tyr
    250                 255                 260

CTG GCC TCC TAC AAT GCC TTC CTG GCT GCC ACC AAG TGG ATC AAC TCG     912
Leu Ala Ser Tyr Asn Ala Phe Leu Ala Ala Thr Lys Trp Ile Asn Ser
265                 270                 275

ATT CCC ACT CCC CGC CTG GCC TGC GAG GTG TTC GCT GAG GCT ATC GCC     960
```

```
Ile Pro Thr Pro Arg Leu Ala Cys Glu Val Phe Ala Glu Ala Ile Ala
280                 285                 290                 295

GCT AAC TCC ACC CTG GTC GCT GAG TAGTAG                               990
Ala Asn Ser Thr Leu Val Ala Glu
                300
```

(2) INFORMATION FOR SEQ ID NO:2:

(i) SEQUENCE CHARACTERISTICS:
        (A) LENGTH: 327 amino acids
        (B) TYPE: amino acids
        (D) TOPOLOGY: linear (ii) MOLECULE TYPE: protein (xi) SEQUENCE DESCRIPTION: SEQ ID NO:2:

```
Met Ala Thr Lys Ile Leu Ala Leu Leu Ala Leu Leu Ala Leu Leu Val
                -20                 -15                 -10

Ser Ala Thr Asn Ala Phe Ile Ile Pro His Leu Arg Leu Gly Leu Val
                -5              -1   1                   5

Phe Thr Ser Asp Asn Asn Glu Arg Ala Leu Gln Asn Ser Gly Leu Tyr
        10                  15                  20

Ser Pro Asp Ser Glu Asp Ser Ser Val Asp Ile Ala Gly Arg Arg Trp
25                  30                  35                  40

His Ser Gly Thr Leu Asn Gly Ser Ser Ile Val Tyr Val Lys Thr Gly
                45                  50                  55

Ser His Ser Val Asn Met Ala Thr Leu Gln Ile Leu Leu Ala Arg
                60                  65                  70

Trp Ser Ile His Gly Val Ile Tyr Phe Gly Asn Ala Gly Ser Leu Asp
        75                  80                  85

Lys Lys Thr Met Val Pro Gly Asp Val Ser Val Pro Gln Ala Val Ala
        90                  95                  100

Phe Thr Gly Val Cys Asn Trp Lys Lys Trp Arg Ser Glu Lys Gly Lys
105                 110                 115                 120

Leu Val Phe Gly Asp Trp Asn Tyr Pro Glu Asn Gly Glu Asn Leu Leu
                125                 130                 135

Gly Thr Val Glu Tyr Glu Lys Ile Lys Met Phe Ser Pro Ser Asp Ala
                140                 145                 150

Pro Lys Glu Val Phe Trp Leu Pro Ile Thr Lys Ser Trp Tyr Asn Ala
        155                 160                 165

Ala Thr Glu Ala Leu Lys Asp Met Lys Leu Arg Lys Cys Tyr Ser Asp
        170                 175                 180

Gly Cys Leu Pro Gly Glu Pro Lys Val Val Phe Gly Ser Lys Ser Ser
185                 190                 195                 200

Thr Ser Asp Trp Tyr Val Arg Asn Lys Ala Tyr Gly Asp Trp Leu Asn
                205                 210                 215

Asp Asn Trp Asp Ala Lys Thr Ala Asp Thr Ser Ala Ser Val Ala
                220                 225                 230

Leu Thr Ser Leu Ser Asn Glu Lys Leu Phe Val Val Phe Gln Gly Val
        235                 240                 245

Ser Asn Val Ala Gly Glu Thr Ser Ser Asn Ser Arg Val Ser Tyr Leu
250                 255                 260

Ala Ser Tyr Asn Ala Phe Leu Ala Ala Thr Lys Trp Ile Asn Ser Ile
265                 270                 275                 280

Pro Thr Pro Arg Leu Ala Cys Glu Val Phe Ala Glu Ala Ile Ala Ala
                285                 290                 295
```

```
Asn Ser Thr Leu Val Ala Glu
        300
```

(2) INFORMATION FOR SEQ ID NO:3:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
ACGACCTGGC GAAGAAGAAG AAGGCGGCCG CCGCTGCAGA CCCACAGGCC GACACGAAG      59
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
CATGCCGGCC AGTGAATTCG G                                                21
```

(2) INFORMATION FOR SEQ ID NO:5:

(i) SEQUENCE CHARACTERISTICS:
        (A) LENGTH: 987 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
TCCCTCTAGA TGCGGCCTAA TTAATTAAGC TTAAAAGGAG GAAAAAAATT ATG AAA        56
                                                      Met Lys
                                                        1

AGA ATA GTG CCA AAG TTC ACT GAA ATC TTC CCC GTG GAG GAC GCG AAC      104
Arg Ile Val Pro Lys Phe Thr Glu Ile Phe Pro Val Glu Asp Ala Asn
        5                  10                  15

TAC CCT TAC AGC GCC TTC ATC GCG TCG GTC CGG AAA GAC GAC GTG ATC      152
Tyr Pro Tyr Ser Ala Phe Ile Ala Ser Val Arg Lys Asp Asp Val Ile
 20                  25                  30

AAA CAC TGC ACC GAC CAT AAA GGG ATC TTC CAG CCC GTG CTG CCA CCG      200
Lys His Cys Thr Asp His Lys Gly Ile Phe Gln Pro Val Leu Pro Pro
 35                  40                  45                  50

GAG AAG AAG GTC CCG GAG CTA TGG TTC TAC ACA GAG CTC AAA ACT AGG      248
Glu Lys Lys Val Pro Glu Leu Trp Phe Tyr Thr Glu Leu Lys Thr Arg
             55                  60                  65

ACC AGC TCC ATC ACG CTC GCC ATA CGC ATG GAC AAC CTG TAC CTC GTG      296
Thr Ser Ser Ile Thr Leu Ala Ile Arg Met Asp Asn Leu Tyr Leu Val
         70                  75                  80

GGC TTC AGG ACC CCG GGC GGG GTG TGG TGG GAG TTC GGC AAG GAC GGC      344
Gly Phe Arg Thr Pro Gly Gly Val Trp Trp Glu Phe Gly Lys Asp Gly
     85                  90                  95

GAC ACC CAC CTC CTC GGC GAC AAC CCC AGG TGG CTC GGC TTC GGC GGC      392
Asp Thr His Leu Leu Gly Asp Asn Pro Arg Trp Leu Gly Phe Gly Gly
100                 105                 110

AGG TAC CAG GAC CTC ATC GGC AAC AAG GGT CTG GAG ACC GTC ACC ATG      440
```

```
-continued

Arg Tyr Gln Asp Leu Ile Gly Asn Lys Gly Leu Glu Thr Val Thr Met
115                 120                 125                 130

GGC CGC GCC GAA ATG ACC AGG GCC GTC AAC GAC CTG GCG AAG AAG AAG      488
Gly Arg Ala Glu Met Thr Arg Ala Val Asn Asp Leu Ala Lys Lys Lys
                135                 140                 145

AAG GCG GCC GCC GCT GCA GAC CCA CAG GCC GAC ACG AAG AGC AAG CTG      536
Lys Ala Ala Ala Ala Ala Asp Pro Gln Ala Asp Thr Lys Ser Lys Leu
            150                 155                 160

GTG AAG CTG GTG GTC ATG GTG TGC GAG GGG CTG CGG TTC AAC ACC GTG      584
Val Lys Leu Val Val Met Val Cys Glu Gly Leu Arg Phe Asn Thr Val
        165                 170                 175

TCC CGC ACG GTG GAC GCG GGG TTC AAC AGC CAG CAC GGG GTG ACC TTG      632
Ser Arg Thr Val Asp Ala Gly Phe Asn Ser Gln His Gly Val Thr Leu
    180                 185                 190

ACC GTG ACG CAG GGG AAG CAG GTG CAG AAG TGG GAC AGG ATC TCC AAG      680
Thr Val Thr Gln Gly Lys Gln Val Gln Lys Trp Asp Arg Ile Ser Lys
195                 200                 205                 210

GCG GCC TTC GAG TGG GCT GAC CAC CCC ACC GCT GTG ATC CCC GAC ATG      728
Ala Ala Phe Glu Trp Ala Asp His Pro Thr Ala Val Ile Pro Asp Met
                215                 220                 225

CAG AAG CTT GGC ATC AAG GAT AAG AAC GAA GCA GCG AGG ATC GTT GCG      776
Gln Lys Leu Gly Ile Lys Asp Lys Asn Glu Ala Ala Arg Ile Val Ala
            230                 235                 240

CTC GTT AAG AAT CAA ACT ACT GCC GCT GCC GCT ACT GCT GGA TCC GCC      824
Leu Val Lys Asn Gln Thr Thr Ala Ala Ala Ala Thr Ala Gly Ser Ala
        245                 250                 255

TGATCAATGC AACGACACAT CATGATCTGC TGCTGCACTT TACTATGTTC GTATACAAAT    884

AAATACACCC GGCGTACGCG GTGTTCCTTA TATGGTCTAA AATGTAGCCA GTAAATTTTA    944

AACTACTTTC TCGTGCCGAA TTCACTGGCC GGCATGCTAT ATA                      987

(2) INFORMATION FOR SEQ ID NO:6:

(i) SEQUENCE CHARACTERISTICS:
        (A) LENGTH: 258 amino acids
        (B) TYPE: amino acids
        (D) TOPOLOGY: linear (ii) MOLECULE TYPE: protein (xi) SEQUENCE DESCRIPTION: SEQ ID NO:6:

Met Lys Arg Ile Val Pro Lys Phe Thr Glu Ile Phe Pro Val Glu Asp
1               5                   10                  15

Ala Asn Tyr Pro Tyr Ser Ala Phe Ile Ala Ser Val Arg Lys Asp Asp
                20                  25                  30

Val Ile Lys His Cys Thr Asp His Lys Gly Ile Phe Gln Pro Val Leu
            35                  40                  45

Pro Pro Glu Lys Lys Val Pro Glu Leu Trp Phe Tyr Thr Glu Leu Lys
        50                  55                  60

Thr Arg Thr Ser Ser Ile Thr Leu Ala Ile Arg Met Asp Asn Leu Tyr
65                  70                  75                  80

Leu Val Gly Phe Arg Thr Pro Gly Gly Val Trp Trp Glu Phe Gly Lys
                85                  90                  95

Asp Gly Asp Thr His Leu Leu Gly Asp Asn Pro Arg Trp Leu Gly Phe
                100                 105                 110

Gly Gly Arg Tyr Gln Asp Leu Ile Gly Asn Lys Gly Leu Glu Thr Val
            115                 120                 125

Thr Met Gly Arg Ala Glu Met Thr Arg Ala Val Asn Asp Leu Ala Lys
        130                 135                 140
```

```
Lys Lys Lys Ala Ala Ala Ala Asp Pro Gln Ala Asp Thr Lys Ser
145                 150                 155                 160

Lys Leu Val Lys Leu Val Val Met Val Cys Glu Gly Leu Arg Phe Asn
            165                 170                 175

Thr Val Ser Arg Thr Val Asp Ala Gly Phe Asn Ser Gln His Gly Val
            180                 185                 190

Thr Leu Thr Val Thr Gln Gly Lys Gln Val Gln Lys Trp Asp Arg Ile
            195                 200                 205

Ser Lys Ala Ala Phe Glu Trp Ala Asp His Pro Thr Ala Val Ile Pro
        210                 215                 220

Asp Met Gln Lys Leu Gly Ile Lys Asp Lys Asn Glu Ala Ala Arg Ile
225                 230                 235                 240

Val Ala Leu Val Lys Asn Gln Thr Thr Ala Ala Ala Thr Ala Gly
                245                 250                 255

Ser Ala (2) INFORMATION FOR SEQ ID NO:7:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GGCGGCCGCC ACACTGAAGA AGAAGAAGGT GAAGATGCAG ATGCAGATGC CGAAGGCCGC    60

TAAGCTGGCG GCGGCTGCA                                                79

(2) INFORMATION FOR SEQ ID NO:8:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GCCGCCGCCA GCTTAGCGGC CTTCGGCATC TGCATCTGCA TCTTCACCTT CTTCTTCTTC    60

AGTGTGGCGG CC                                                       72

(2) INFORMATION FOR SEQ ID NO:9:

(i) SEQUENCE CHARACTERISTICS:
        (A) LENGTH: 1059 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TCCCTCTAGA TGCGGCCTAA TTAATTAAGC TTAAAAGGAG GAAAAAATT ATG AAA        56
                                                      Met Lys
                                                        1

AGA ATA GTG CCA AAG TTC ACT GAA ATC TTC CCC GTG GAG GAC GCG AAC    104
Arg Ile Val Pro Lys Phe Thr Glu Ile Phe Pro Val Glu Asp Ala Asn
      5                  10                  15
```

```
TAC CCT TAC AGC GCC TTC ATC GCG TCG GTC CGG AAA GAC GTG ATC AAA      152
Tyr Pro Tyr Ser Ala Phe Ile Ala Ser Val Arg Lys Asp Val Ile Lys
 20                  25                  30

CAC TGC ACC GAC CAT AAA GGG ATC TTC CAG CCC GTG CTG CCA CCG GAG      200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC      248
Lys Lys Val Pro Glu Leu Trp Phe Tyr Thr Glu Leu Lys Thr Arg Thr
             55                  60                  65

AGC TCC ATC ACG CTC GCC ATA CGC ATG GAC AAC CTG TAC CTC GTG GGC      296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC      344
Phe Arg Thr Pro Gly Gly Val Trp Trp Glu Phe Gly Lys Asp Gly Asp
                 85                  90                  95

ACC CAC CTC CTC GGC GAC AAC CCC AGG TGG CTC GGC TTC GGC GGC AGG      392
Thr His Leu Leu Gly Asp Asn Pro Arg Trp Leu Gly Phe Gly Gly Arg
100                 105                 110

TAC CAG GAC CTC ATC GGC AAC AAG GGT CTG GAG ACC GTC ACC ATG GGC      440
Tyr Gln Asp Leu Ile Gly Asn Lys Gly Leu Glu Thr Val Thr Met Gly
115                 120                 125                 130

CGC GCC GAA ATG ACC AGG GCC GTC AAC GAC CTG GCG AAG AAG AAG AAG      488
Arg Ala Glu Met Thr Arg Ala Val Asn Asp Leu Ala Lys Lys Lys Lys
                135                 140                 145

GCG GCG GCC GCC ACA CTG AAG AAG AAG AAG GTG AAG ATG CAG ATG CAG      536
Ala Ala Ala Ala Thr Leu Lys Lys Lys Lys Val Lys Met Gln Met Gln
            150                 155                 160

ATG CCG AAG GCC GCT AAG CTG GCG GCG GCT GCA GAC CCA CAG GCC GAC      584
Met Pro Lys Ala Ala Lys Leu Ala Ala Ala Ala Asp Pro Gln Ala Asp
        165                 170                 175

ACG AAG AGC AAG CTG GTG AAG CTG GTG GTC ATG GTG TGC GAG GGG CTG      632
Thr Lys Ser Lys Leu Val Lys Leu Val Val Met Val Cys Glu Gly Leu
180                 185                 190

CGG TTC AAC ACC GTG TCC CGC ACG GTG GAC GCG GGG TTC AAC AGC CAG      680
Arg Phe Asn Thr Val Ser Arg Thr Val Asp Ala Gly Phe Asn Ser Gln
195                 200                 205                 210

CAC GGG GTG ACC TTG ACC GTG ACG CAG GGG AAG CAG GTG CAG AAG TGG      728
His Gly Val Thr Leu Thr Val Thr Gln Gly Lys Gln Val Gln Lys Trp
                215                 220                 225

GAC AGG ATC TCC AAG GCG GCC TTC GAG TGG GCT GAC CAC CCC ACC GCT      776
Asp Arg Ile Ser Lys Ala Ala Phe Glu Trp Ala Asp His Pro Thr Ala
            230                 235                 240

GTG ATC CCC GAC ATG CAG AAG CTT GGC ATC AAG GAT AAG AAC GAA GCA      824
Val Ile Pro Asp Met Gln Lys Leu Gly Ile Lys Asp Lys Asn Glu Ala
        245                 250                 255

GCG AGG ATC GTT GCG CTC GTT AAG AAT CAA ACT ACT GCC GCT GCC GCT      872
Ala Arg Ile Val Ala Leu Val Lys Asn Gln Thr Thr Ala Ala Ala Ala
260                 265                 270

ACT GCT GGA TCC GCC TGATCAATGC AACGACACAT CATGATCTGC ATCTGCTGCT      927
Thr Ala Gly Ser Ala
275

GCACTTAATT ACTATGTTCG TATACAAATA AATACACCCG GCGTACGCGG TGTTCCTTAT     987

ATGGTCTAAA ATGTAGCCAG TAAATTTTAA ACTACTTTCT CGTGCCGAAT TCACTGGCCG    1047

GCATGCTATA TA                                                        1059
```

(2) INFORMATION FOR SEQ ID NO:10:

(i) SEQUENCE CHARACTERISTICS:
        (A) LENGTH: 279 amino acids

```
        (B) TYPE: amino acids
        (D) TOPOLOGY: linear (ii) MOLECULE TYPE: protein (xi) SEQUENCE DESCRIPTION: SEQ ID NO:10:

Met Lys Arg Ile Val Pro Lys Phe Thr Glu Ile Phe Pro Val Glu Asp
1               5                   10                  15

Ala Asn Tyr Pro Tyr Ser Ala Phe Ile Ala Ser Val Arg Lys Asp Val
            20                  25                  30

Ile Lys His Cys Thr Asp His Lys Gly Ile Phe Gln Pro Val Leu Pro
        35                  40                  45

Pro Glu Lys Lys Val Pro Glu Leu Trp Phe Tyr Thr Glu Leu Lys Thr
    50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
            100                 105                 110

Gly Arg Tyr Gln Asp Leu Ile Gly Asn Lys Gly Leu Glu Thr Val Thr
        115                 120                 125

Met Gly Arg Ala Glu Met Thr Arg Ala Val Asn Asp Leu Ala Lys Lys
130                 135                 140

Lys Lys Ala Ala Ala Thr Leu Lys Lys Lys Val Lys Met Gln
145                 150                 155                 160

Met Gln Met Pro Lys Ala Ala Lys Leu Ala Ala Ala Asp Pro Gln
                165                 170                 175

Ala Asp Thr Lys Ser Lys Leu Val Lys Leu Val Val Met Val Cys Glu
            180                 185                 190

Gly Leu Arg Phe Asn Thr Val Ser Arg Thr Val Asp Ala Gly Phe Asn
                195                 200                 205

Ser Gln His Gly Val Thr Leu Thr Val Thr Gln Gly Lys Gln Val Gln
        210                 215                 220

Lys Trp Asp Arg Ile Ser Lys Ala Ala Phe Glu Trp Ala Asp His Pro
225                 230                 235                 240

Thr Ala Val Ile Pro Asp Met Gln Lys Leu Gly Ile Lys Asp Lys Asn
                245                 250                 255

Glu Ala Ala Arg Ile Val Ala Leu Val Lys Asn Gln Thr Thr Ala Ala
            260                 265                 270

Ala Ala Thr Ala Gly Ser Ala
        275

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CAGGACCTCA TCGGCAACAA GGGTCTGGAG ACCGTCAG                              38

(2) INFORMATION FOR SEQ ID NO:12:
```

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:12:

```
CATGGTGACG GTCTCCAGAC CCTTGTTGCC GATGAGGTCC TGGTAC                    46
```

(2) INFORMATION FOR SEQ ID NO:13:

(i) SEQUENCE CHARACTERISTICS:
    (A) LENGTH: 1053 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:13:

```
TCCCTCTAGA TGCGGCCTAA TTAATTAAGC TTAAAAGGAG GAAAAAAATT ATG AAA        56
                                                       Met Lys
                                                         1

AGA ATA GTG CCA AAG TTC ACT GAA ATC TTC CCC GTG GAG GAC GCG AAC      104
Arg Ile Val Pro Lys Phe Thr Glu Ile Phe Pro Val Glu Asp Ala Asn
          5                  10                  15

TAC CCT TAC AGC GCC TTC ATC GCG TCG GTC CGG AAA GAC GTG ATC AAA      152
Tyr Pro Tyr Ser Ala Phe Ile Ala Ser Val Arg Lys Asp Val Ile Lys
 20                  25                  30

CAC TGC ACC GAC CAT AAA GGG ATC TTC CAG CCC GTG CTG CCA CCG GAG      200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC      248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC      296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC      344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG      392
Thr His Leu Leu Gly Asp Asn Pro Arg Trp Leu Gly Phe Gly Gly Arg
    100                 105                 110

TAC CAG GAC CTC ATC GGC AAC AAG GGT CTG GAG ACC GTC AGC ATG GGC      440
Tyr Gln Asp Leu Ile Gly Asn Lys Gly Leu Glu Thr Val Ser Met Gly
115                 120                 125                 130

CGC GCC GAA ATG ACC AGG GCC GTC AAC GAC CTG GCG AAG AAG AAG AAG      488
Arg Ala Glu Met Thr Arg Ala Val Asn Asp Leu Ala Lys Lys Lys Lys
                135                 140                 145

GCG GCG GCC GCC ACA CTG AAG AAG AAG AAG GTG AAG ATG CAG ATG CAG      536
Ala Ala Ala Ala Thr Leu Lys Lys Lys Lys Val Lys Met Gln Met Gln
            150                 155                 160

ATG CCG AAG GCC GCT AAG CTG GCG GCG GCT GCA GAC CCA CAG GCC GAC      584
Met Pro Lys Ala Ala Lys Leu Ala Ala Ala Ala Asp Pro Gln Ala Asp
        165                 170                 175

ACG AAG AGC AAG CTG GTG AAG CTG GTG GTC ATG GTG TGC GAG GGG CTG      632
Thr Lys Ser Lys Leu Val Lys Leu Val Val Met Val Cys Glu Gly Leu
    180                 185                 190

CGG TTC AAC ACC GTG TCC CGC ACG GTG GAC GCG GGG TTC AAC AGC CAG      680
Arg Phe Asn Thr Val Ser Arg Thr Val Asp Ala Gly Phe Asn Ser Gln
```

-continued

```
                195                     200                     205                     210
CAC GGG GTG ACC TTG ACC GTG ACG CAG GGG AAG CAG GTG CAG AAG TGG            728
His Gly Val Thr Leu Thr Val Thr Gln Gly Lys Gln Val Gln Lys Trp
                        215                     220                     225

GAC AGG ATC TCC AAG GCG GCC TTC GAG TGG GCT GAC CAC CCC ACC GCT            776
Asp Arg Ile Ser Lys Ala Ala Phe Glu Trp Ala Asp His Pro Thr Ala
                        230                     235                     240

GTG ATC CCC GAC ATG CAG AAG CTT GGC ATC AAG GAT AAG AAC GAA GCA            824
Val Ile Pro Asp Met Gln Lys Leu Gly Ile Lys Asp Lys Asn Glu Ala
                        245                     250                     255

GCG AGG ATC GTT GCG CTC GTT AAG AAT CAA ACT ACT GCC GCT GCC GCT            872
Ala Arg Ile Val Ala Leu Val Lys Asn Gln Thr Thr Ala Ala Ala Ala
                        260                     265                     270

ACT GCT GGA TCC GCC TGATCAATGC AACGACACAT CATGATCTGC TGCTGCACTT            927
Thr Ala Gly Ser Ala
275

AATTACTATG TTCGTATACA AATAAATACA CCCGGCGTAC GCGGTGTTCC TTATATGGTC          987

TAAAATGTAG CCAGTAAATT TTAAACTACT TTCTCGTGCC GAATTCACTG GCCGGCATGC          1047

TATATA                                                                    1053
```

(2) INFORMATION FOR SEQ ID NO:14:

(i) SEQUENCE CHARACTERISTICS:
        (A) LENGTH: 279 amino acids
        (B) TYPE: amino acids
        (D) TOPOLOGY: linear (ii) MOLECULE TYPE: protein (xi) SEQUENCE DESCRIPTION: SEQ ID NO:14:

```
Met Lys Arg Ile Val Pro Lys Phe Thr Glu Ile Phe Pro Val Glu Asp
1               5                   10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
                100                 105                 110

Gly Arg Tyr Gln Asp Leu Ile Gly Asn Lys Gly Leu Glu Thr Val Ser
            115                 120                 125

Met Gly Arg Ala Glu Met Thr Arg Ala Val Asn Asp Leu Ala Lys Lys
        130                 135                 140

Lys Lys Ala Ala Ala Thr Leu Lys Lys Lys Val Lys Met Gln
145                 150                 155                 160

Met Gln Met Pro Lys Ala Ala Lys Leu Ala Ala Ala Asp Pro Gln
                165                 170                 175

Ala Asp Thr Lys Ser Lys Leu Val Lys Leu Val Val Met Val Cys Glu
            180                 185                 190

Gly Leu Arg Phe Asn Thr Val Ser Arg Thr Val Asp Ala Gly Phe Asn
        195                 200                 205
```

```
Ser Gln His Gly Val Thr Leu Thr Val Thr Gln Gly Lys Gln Val Gln
    210                 215                 220

Lys Trp Asp Arg Ile Ser Lys Ala Ala Phe Glu Trp Ala Asp His Pro
225                 230                 235                 240

Thr Ala Val Ile Pro Asp Met Gln Lys Leu Gly Ile Lys Asp Lys Asn
                245                 250                 255

Glu Ala Ala Arg Ile Val Ala Leu Val Lys Asn Gln Thr Thr Ala Ala
            260                 265                 270

Ala Ala Thr Ala Gly Ser Ala
        275

(2) INFORMATION FOR SEQ ID NO:15:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GTTGCGCTCG TTAAGAATCA AACCACCGCC GCTGCCGACG CGTCCGCTAA GAACAAGAAG      60

AAGAAGAGCA TGCCCGCCTA GTAGCTCGAG TATATA                                96

(2) INFORMATION FOR SEQ ID NO:16:

(i) SEQUENCE CHARACTERISTICS:
        (A) LENGTH: 944 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TCCCTCTAGA TGCGGCCTAA TTAATTAAGC TTAAAAGGAG GAAAAAAATT ATG AAA         56
                                                        Met Lys
                                                         1

AGA ATA GTG CCA AAG TTC ACT GAA ATC TTC CCC GTG GAG GAC GCG AAC       104
Arg Ile Val Pro Lys Phe Thr Glu Ile Phe Pro Val Glu Asp Ala Asn
        5                  10                  15

TAC CCT TAC AGC GCC TTC ATC GCG TCG GTC CGG AAA GAC GTG ATC AAA       152
Tyr Pro Tyr Ser Ala Phe Ile Ala Ser Val Arg Lys Asp Val Ile Lys
 20                  25                  30

CAC TGC ACC GAC CAT AAA GGG ATC TTC CAG CCC GTG CTG CCA CCG GAG       200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC       248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC       296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC       344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG       392
Thr His Leu Leu Gly Asp Asn Pro Arg Trp Leu Gly Phe Gly Gly Arg
     100                 105                 110

TAC CAG GAC CTC ATC GGC AAC AAG GGT CTG GAG ACC GTC AGC ATG GGC       440
Tyr Gln Asp Leu Ile Gly Asn Lys Gly Leu Glu Thr Val Ser Met Gly
```

```
     115              120              125              130
CGC GCC GAA ATG ACC AGG GCC GTC AAC GAC CTG GCG AAG AAG AAG AAG      488
Arg Ala Glu Met Thr Arg Ala Val Asn Asp Leu Ala Lys Lys Lys Lys
                      135              140              145

GCG GCG GCC GCC ACA CTG AAG AAG AAG AAG GTG AAG ATG CAG ATG CAG      536
Ala Ala Ala Ala Thr Leu Lys Lys Lys Lys Val Lys Met Gln Met Gln
            150              155              160

ATG CCG AAG GCC GCT AAG CTG GCG GCG GCT GCA GAC CCA CAG GCC GAC      584
Met Pro Lys Ala Ala Lys Leu Ala Ala Ala Ala Asp Pro Gln Ala Asp
            165              170              175

ACG AAG AGC AAG CTG GTG AAG CTG GTG GTC ATG GTG TGC GAG GGG CTG      632
Thr Lys Ser Lys Leu Val Lys Leu Val Val Met Val Cys Glu Gly Leu
        180              185              190

CGG TTC AAC ACC GTG TCC CGC ACG GTG GAC GCG GGG TTC AAC AGC CAG      680
Arg Phe Asn Thr Val Ser Arg Thr Val Asp Ala Gly Phe Asn Ser Gln
195              200              205              210

CAC GGG GTG ACC TTG ACC GTG ACG CAG GGG AAG CAG GTG CAG AAG TGG      728
His Gly Val Thr Leu Thr Val Thr Gln Gly Lys Gln Val Gln Lys Trp
                215              220              225

GAC AGG ATC TCC AAG GCG GCC TTC GAG TGG GCT GAC CAC CCC ACC GCT      776
Asp Arg Ile Ser Lys Ala Ala Phe Glu Trp Ala Asp His Pro Thr Ala
            230              235              240

GTG ATC CCC GAC ATG CAG AAG CTT GGC ATC AAG GAT AAG AAC GAA GCA      824
Val Ile Pro Asp Met Gln Lys Leu Gly Ile Lys Asp Lys Asn Glu Ala
            245              250              255

GCG AGG ATC GTT GCG CTC GTT AAG AAT CAA ACC ACC GCC GCT GCC GAC      872
Ala Arg Ile Val Ala Leu Val Lys Asn Gln Thr Thr Ala Ala Ala Asp
        260              265              270

GCG TCC GCT AAG AAC AAG AAG AAG AAG AGC ATG CCC GCC TAGTAGCTCG       921
Ala Ser Ala Lys Asn Lys Lys Lys Lys Ser Met Pro Ala
275              280              285

AGTATATACC CCCTAGCTAT ATA                                            944
```

(2) INFORMATION FOR SEQ ID NO:17:

(i) SEQUENCE CHARACTERISTICS:
        (A) LENGTH: 287 amino acids
        (B) TYPE: amino acids
        (D) TOPOLOGY: linear (ii) MOLECULE TYPE: protein (xi) SEQUENCE DESCRIPTION: SEQ ID NO:17:

```
Met Lys Arg Ile Val Pro Lys Phe Thr Glu Ile Phe Pro Val Glu Asp
1               5                   10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
    50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
            100                 105                 110

Gly Arg Tyr Gln Asp Leu Ile Gly Asn Lys Gly Leu Glu Thr Val Ser
        115                 120                 125
```

```
Met Gly Arg Ala Glu Met Thr Arg Ala Val Asn Asp Leu Ala Lys Lys
    130                 135                 140
Lys Lys Ala Ala Ala Thr Leu Lys Lys Lys Val Lys Met Gln
145                 150                 155                 160
Met Gln Met Pro Lys Ala Ala Lys Leu Ala Ala Ala Asp Pro Gln
                165                 170                 175
Ala Asp Thr Lys Ser Lys Leu Val Lys Leu Val Val Met Val Cys Glu
            180                 185                 190
Gly Leu Arg Phe Asn Thr Val Ser Arg Thr Val Asp Ala Gly Phe Asn
            195                 200                 205
Ser Gln His Gly Val Thr Leu Thr Val Thr Gln Gly Lys Gln Val Gln
    210                 215                 220
Lys Trp Asp Arg Ile Ser Lys Ala Ala Phe Glu Trp Ala Asp His Pro
225                 230                 235                 240
Thr Ala Val Ile Pro Asp Met Gln Lys Leu Gly Ile Lys Asp Lys Asn
                245                 250                 255
Glu Ala Ala Arg Ile Val Ala Leu Val Lys Asn Gln Thr Thr Ala Ala
            260                 265                 270
Ala Asp Ala Ser Ala Lys Asn Lys Lys Lys Ser Met Pro Ala
        275                 280                 285

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

ATATATAGCA TGCCCATTGG TGATGATGTC CCAATACTC                              39

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CCACTACTAT CACGTTTCAC TATCGAGCTC ATATAT                                 36

(2) INFORMATION FOR SEQ ID NO:20:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

ATA TAT AGC ATG CCC ATT GGT GAT GAT GTC CCA ATA CTC GGG GGC ATT        48
Ile Tyr Ser Met Pro Ile Gly Asp Asp Val Pro Ile Leu Gly Gly Ile
1               5                   10                  15
ATC AAT GTT CAA GGC ATA AAC AGC CTT GTG TTC CAA GAT CTT GCT CGT        96
```

```
                                                                              -continued Ile Asn Val Gln Gly Ile Asn Ser Leu Val Phe Gln Asp Leu Ala Arg
             20                  25                  30

TTT GCT GTT CAG GAT CAT AAT AAG AAA GAG AAG GCT CAT TTG GAG TTT              144
Phe Ala Val Gln Asp His Asn Lys Lys Glu Lys Ala His Leu Glu Phe
         35                  40                  45

GTA GAA GTT TTG AAT GTG AAG GAA CAA GTT GTT GCG GGA ATG ATG TAC              192
Val Glu Val Leu Asn Val Lys Glu Gln Val Val Ala Gly Met Met Tyr
 50                  55                  60

TAT ATA ACA CTT GCG GCA ACT GAT GCT GGA AAG AAG AAA ATA TAT GAA              240
Tyr Ile Thr Leu Ala Ala Thr Asp Ala Gly Lys Lys Lys Ile Tyr Glu
 65                  70                  75                  80

GCT AAG ATT TGG GTG AAA GAA TGG GAG GAC TTC AAG AAA GTT GTA GAG              288
Ala Lys Ile Trp Val Lys Glu Trp Glu Asp Phe Lys Lys Val Val Glu
                 85                  90                  95

TTC AAG CTT GTT GGT GAT GAT AGT GCA AAG TGATAGCTCG AGTATATA                  336
Phe Lys Leu Val Gly Asp Asp Ser Ala Lys
            100                 105

(2) INFORMATION FOR SEQ ID NO:21:

(i) SEQUENCE CHARACTERISTICS:
        (A) LENGTH:  106 amino acids
        (B) TYPE:  amino acids
        (D) TOPOLOGY:  linear (ii) MOLECULE TYPE:  protein (xi) SEQUENCE DESCRIPTION: SEQ ID NO:21:

Ile Tyr Ser Met Pro Ile Gly Asp Asp Val Pro Ile Leu Gly Gly Ile
 1               5                  10                  15

Ile Asn Val Gln Gly Ile Asn Ser Leu Val Phe Gln Asp Leu Ala Arg
             20                  25                  30

Phe Ala Val Gln Asp His Asn Lys Lys Glu Lys Ala His Leu Glu Phe
         35                  40                  45

Val Glu Val Leu Asn Val Lys Glu Gln Val Val Ala Gly Met Met Tyr
 50                  55                  60

Tyr Ile Thr Leu Ala Ala Thr Asp Ala Gly Lys Lys Lys Ile Tyr Glu
 65                  70                  75                  80

Ala Lys Ile Trp Val Lys Glu Trp Glu Asp Phe Lys Lys Val Val Glu
                 85                  90                  95

Phe Lys Leu Val Gly Asp Asp Ser Ala Lys
            100                 105

(2) INFORMATION FOR SEQ ID NO:22:

(i) SEQUENCE CHARACTERISTICS:
        (A) LENGTH:  1244 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO:22:

TCCCTCTAGA TGCGGCCTAA TTAATTAAGC TTAAAAGGAG GAAAAAAATT ATG AAA               56
                                                         Met Lys
                                                          1

AGA ATA GTG CCA AAG TTC ACT GAA ATC TTC CCC GTG GAG GAC GCG AAC              104
Arg Ile Val Pro Lys Phe Thr Glu Ile Phe Pro Val Glu Asp Ala Asn
         5                   10                  15

TAC CCT TAC AGC GCC TTC ATC GCG TCG GTC CGG AAA GAC GTG ATC AAA              152
Tyr Pro Tyr Ser Ala Phe Ile Ala Ser Val Arg Lys Asp Val Ile Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 20  |     |     |     | 25  |     |     |     | 30  |     |     |     |     |     |     |      |
| CAC | TGC | ACC | GAC | CAT | AAA | GGG | ATC | TTC | CAG | CCC | GTG | CTG | CCA | CCG | GAG | 200  |
| His | Cys | Thr | Asp | His | Lys | Gly | Ile | Phe | Gln | Pro | Val | Leu | Pro | Pro | Glu |      |
| 35  |     |     |     |     | 40  |     |     |     |     | 45  |     |     |     |     | 50  |      |
| AAG | AAG | GTC | CCG | GAG | CTA | TGG | TTC | TAC | ACA | GAG | CTC | AAA | ACT | AGG | ACC | 248  |
| Lys | Lys | Val | Pro | Glu | Leu | Trp | Phe | Tyr | Thr | Glu | Leu | Lys | Thr | Arg | Thr |      |
|     |     |     |     |     | 55  |     |     |     |     | 60  |     |     |     |     | 65  |      |
| AGC | TCC | ATC | ACG | CTC | GCC | ATA | CGC | ATG | GAC | AAC | CTG | TAC | CTC | GTG | GGC | 296  |
| Ser | Ser | Ile | Thr | Leu | Ala | Ile | Arg | Met | Asp | Asn | Leu | Tyr | Leu | Val | Gly |      |
|     |     |     | 70  |     |     |     |     | 75  |     |     |     |     | 80  |     |     |      |
| TTC | AGG | ACC | CCG | GGC | GGG | GTG | TGG | TGG | GAG | TTC | GGC | AAG | GAC | GGC | GAC | 344  |
| Phe | Arg | Thr | Pro | Gly | Gly | Val | Trp | Trp | Glu | Phe | Gly | Lys | Asp | Gly | Asp |      |
|     |     | 85  |     |     |     |     | 90  |     |     |     |     | 95  |     |     |     |      |
| ACC | CAC | CTC | CTC | GGC | GAC | AAC | CCC | AGG | TGG | CTC | GGC | TTC | GGC | GGC | AGG | 392  |
| Thr | His | Leu | Leu | Gly | Asp | Asn | Pro | Arg | Trp | Leu | Gly | Phe | Gly | Gly | Arg |      |
|     | 100 |     |     |     |     | 105 |     |     |     |     | 110 |     |     |     |     |      |
| TAC | CAG | GAC | CTC | ATC | GGC | AAC | AAG | GGT | CTG | GAG | ACC | GTC | AGC | ATG | GGC | 440  |
| Tyr | Gln | Asp | Leu | Ile | Gly | Asn | Lys | Gly | Leu | Glu | Thr | Val | Ser | Met | Gly |      |
| 115 |     |     |     |     | 120 |     |     |     |     | 125 |     |     |     |     | 130 |      |
| CGC | GCC | GAA | ATG | ACC | AGG | GCC | GTC | AAC | GAC | CTG | GCG | AAG | AAG | AAG | AAG | 488  |
| Arg | Ala | Glu | Met | Thr | Arg | Ala | Val | Asn | Asp | Leu | Ala | Lys | Lys | Lys | Lys |      |
|     |     |     |     | 135 |     |     |     |     | 140 |     |     |     |     | 145 |     |      |
| GCG | GCG | GCC | GCC | ACA | CTG | AAG | AAG | AAG | AAG | GTG | AAG | ATG | CAG | ATG | CAG | 536  |
| Ala | Ala | Ala | Ala | Thr | Leu | Lys | Lys | Lys | Lys | Val | Lys | Met | Gln | Met | Gln |      |
|     |     |     | 150 |     |     |     |     | 155 |     |     |     |     | 160 |     |     |      |
| ATG | CCG | AAG | GCC | GCT | AAG | CTG | GCG | GCG | GCT | GCA | GAC | CCA | CAG | GCC | GAC | 584  |
| Met | Pro | Lys | Ala | Ala | Lys | Leu | Ala | Ala | Ala | Ala | Asp | Pro | Gln | Ala | Asp |      |
|     |     | 165 |     |     |     |     | 170 |     |     |     |     | 175 |     |     |     |      |
| ACG | AAG | AGC | AAG | CTG | GTG | AAG | CTG | GTG | GTC | ATG | GTG | TGC | GAG | GGG | CTG | 632  |
| Thr | Lys | Ser | Lys | Leu | Val | Lys | Leu | Val | Val | Met | Val | Cys | Glu | Gly | Leu |      |
|     | 180 |     |     |     |     | 185 |     |     |     |     | 190 |     |     |     |     |      |
| CGG | TTC | AAC | ACC | GTG | TCC | CGC | ACG | GTG | GAC | GCG | GGG | TTC | AAC | AGC | CAG | 680  |
| Arg | Phe | Asn | Thr | Val | Ser | Arg | Thr | Val | Asp | Ala | Gly | Phe | Asn | Ser | Gln |      |
| 195 |     |     |     |     | 200 |     |     |     |     | 205 |     |     |     |     | 210 |      |
| CAC | GGG | GTG | ACC | TTG | ACC | GTG | ACG | CAG | GGG | AAG | CAG | GTG | CAG | AAG | TGG | 728  |
| His | Gly | Val | Thr | Leu | Thr | Val | Thr | Gln | Gly | Lys | Gln | Val | Gln | Lys | Trp |      |
|     |     |     |     | 215 |     |     |     |     | 220 |     |     |     |     | 225 |     |      |
| GAC | AGG | ATC | TCC | AAG | GCG | GCC | TTC | GAG | TGG | GCT | GAC | CAC | CCC | ACC | GCT | 776  |
| Asp | Arg | Ile | Ser | Lys | Ala | Ala | Phe | Glu | Trp | Ala | Asp | His | Pro | Thr | Ala |      |
|     |     |     | 230 |     |     |     |     | 235 |     |     |     |     | 240 |     |     |      |
| GTG | ATC | CCC | GAC | ATG | CAG | AAG | CTT | GGC | ATC | AAG | GAT | AAG | AAC | GAA | GCA | 824  |
| Val | Ile | Pro | Asp | Met | Gln | Lys | Leu | Gly | Ile | Lys | Asp | Lys | Asn | Glu | Ala |      |
|     |     | 245 |     |     |     |     | 250 |     |     |     |     | 255 |     |     |     |      |
| GCG | AGG | ATC | GTT | GCG | CTC | GTT | AAG | AAT | CAA | ACC | ACC | GCC | GCT | GCC | GAC | 872  |
| Ala | Arg | Ile | Val | Ala | Leu | Val | Lys | Asn | Gln | Thr | Thr | Ala | Ala | Ala | Asp |      |
|     | 260 |     |     |     |     | 265 |     |     |     |     | 270 |     |     |     |     |      |
| GCG | TCC | GCT | AAG | AAC | AAG | AAG | AAG | AGC | ATG | CCC | ATT | GGT | GAT | GAT | GAT | 920  |
| Ala | Ser | Ala | Lys | Asn | Lys | Lys | Lys | Ser | Met | Pro | Ile | Gly | Asp | Asp | Asp |      |
| 275 |     |     |     |     | 280 |     |     |     |     | 285 |     |     |     |     | 290 |      |
| GTC | CCA | ATA | CTC | GGG | GGC | ATT | ATC | AAT | GTT | CAA | GGC | ATA | AAC | AGC | CTT | 968  |
| Val | Pro | Ile | Leu | Gly | Gly | Ile | Ile | Asn | Val | Gln | Gly | Ile | Asn | Ser | Leu |      |
|     |     |     |     | 295 |     |     |     |     | 300 |     |     |     |     | 305 |     |      |
| GTG | TTC | CAA | GAT | CTT | GCT | CGT | TTT | GCT | GTT | CAG | GAT | CAT | AAT | AAG | AAA | 1016 |
| Val | Phe | Gln | Asp | Leu | Ala | Arg | Phe | Ala | Val | Gln | Asp | His | Asn | Lys | Lys |      |
|     |     |     | 310 |     |     |     |     | 315 |     |     |     |     | 320 |     |     |      |
| GAG | AAG | GCT | CAT | TTG | GAG | TTT | GTA | GAA | GTT | TTG | AAT | GTG | AAG | GAA | CAA | 1064 |
| Glu | Lys | Ala | His | Leu | Glu | Phe | Val | Glu | Val | Leu | Asn | Val | Lys | Glu | Gln |      |
|     |     | 325 |     |     |     |     | 330 |     |     |     |     | 335 |     |     |     |      |
| GTT | GTT | GCG | GGA | ATG | ATG | TAC | TAT | ATA | ACA | CTT | GCG | GCA | ACT | GAT | GCT | 1112 |

```
Val Val Ala Gly Met Met Tyr Tyr Ile Thr Leu Ala Ala Thr Asp Ala
            340                 345                 350

GGA AAG AAG AAA ATA TAT GAA GCT AAG ATT TGG GTG AAA GAA TGG GAG      1160
Gly Lys Lys Lys Ile Tyr Glu Ala Lys Ile Trp Val Lys Glu Trp Glu
355                 360                 365                 370

GAC TTC AAG AAA GTT GTA GAG TTC AAG CTT GTT GGT GAT GAT AGT GCA      1208
Asp Phe Lys Lys Val Val Glu Phe Lys Leu Val Gly Asp Asp Ser Ala
                375                 380                 385

AAG TGATAGCTCG AGTATATACC CCCTAGCTAT ATA                             1244
Lys (2) INFORMATION FOR SEQ ID NO:23:

(i) SEQUENCE CHARACTERISTICS:
        (A) LENGTH: 387 amino acids
        (B) TYPE: amino acids
        (D) TOPOLOGY: linear (ii) MOLECULE TYPE: protein (xi) SEQUENCE DESCRIPTION: SEQ ID NO:23:

Met Lys Arg Ile Val Pro Lys Phe Thr Glu Ile Phe Pro Val Glu Asp
1               5                   10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
                100                 105                 110

Gly Arg Tyr Gln Asp Leu Ile Gly Asn Lys Gly Leu Glu Thr Val Ser
            115                 120                 125

Met Gly Arg Ala Glu Met Thr Arg Ala Val Asn Asp Leu Ala Lys Lys
130                 135                 140

Lys Lys Ala Ala Ala Thr Leu Lys Lys Lys Val Lys Met Gln
145                 150                 155                 160

Met Gln Met Pro Lys Ala Ala Lys Leu Ala Ala Ala Asp Pro Gln
                165                 170                 175

Ala Asp Thr Lys Ser Lys Leu Val Lys Leu Val Val Met Val Cys Glu
            180                 185                 190

Gly Leu Arg Phe Asn Thr Val Ser Arg Thr Val Asp Ala Gly Phe Asn
            195                 200                 205

Ser Gln His Gly Val Thr Leu Thr Val Thr Gln Gly Lys Gln Val Gln
        210                 215                 220

Lys Trp Asp Arg Ile Ser Lys Ala Ala Phe Glu Trp Ala Asp His Pro
225                 230                 235                 240

Thr Ala Val Ile Pro Asp Met Gln Lys Leu Gly Ile Lys Asp Lys Asn
                245                 250                 255

Glu Ala Ala Arg Ile Val Ala Leu Val Lys Asn Gln Thr Thr Ala Ala
            260                 265                 270

Ala Asp Ala Ser Ala Lys Asn Lys Lys Lys Ser Met Pro Ile Gly
            275                 280                 285
```

```
Asp Asp Val Pro Ile Leu Gly Gly Ile Ile Asn Val Gln Gly Ile Asn
    290                 295                 300
Ser Leu Val Phe Gln Asp Leu Ala Arg Phe Ala Val Gln Asp His Asn
305                 310                 315                 320
Lys Lys Glu Lys Ala His Leu Glu Phe Val Glu Val Leu Asn Val Lys
                325                 330                 335
Glu Gln Val Val Ala Gly Met Met Tyr Tyr Ile Thr Leu Ala Ala Thr
                340                 345                 350
Asp Ala Gly Lys Lys Lys Ile Tyr Glu Ala Lys Ile Trp Val Lys Glu
            355                 360                 365
Trp Glu Asp Phe Lys Lys Val Val Glu Phe Lys Leu Val Gly Asp Asp
    370                 375                 380
Ser Ala Lys
385

(2) INFORMATION FOR SEQ ID NO:24:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TCTAGAAAAA GGAGGAAAAA AACCATGGCC AAGATCAAGC TGAAGCCCAA GAAGCTGATG      60

GCCAAGAAGA AGAAGAAGAT CGTCGACCCA AAGTTCACCG AGATCTTCCC CGTGGAGGAC     120

GCGAAC                                                                126

(2) INFORMATION FOR SEQ ID NO:25:

(i) SEQUENCE CHARACTERISTICS:
        (A) LENGTH: 1245 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TCTAGAAAAA GGAGGAAAAC C ATG GCC AAG ATC AAG CTG AAG CCC AAG AAG        51
                        Met Ala Lys Ile Lys Leu Lys Pro Lys Lys
                         1               5                  10

CTG ATG GCC AAG AAG AAG AAG AAG ATC GTC GAC CCA AAG TTC ACC GAG        99
Leu Met Ala Lys Lys Lys Lys Lys Ile Val Asp Pro Lys Phe Thr Glu
                15                  20                  25

ATC TTC CCC GTG GAG GAC GCG AAC TAC CCT TAC AGC GCC TTC ATC GCG       147
Ile Phe Pro Val Glu Asp Ala Asn Tyr Pro Tyr Ser Ala Phe Ile Ala
                30                  35                  40

TCG GTC CGG AAA GAC GTG ATC AAA CAC TGC ACC GAC CAT AAA GGG ATC       195
Ser Val Arg Lys Asp Val Ile Lys His Cys Thr Asp His Lys Gly Ile
                45                  50                  55

TTC CAG CCC GTG CTG CCA CCG GAG AAG AAG GTC CCG GAG CTA TGG TTC       243
Phe Gln Pro Val Leu Pro Pro Glu Lys Lys Val Pro Glu Leu Trp Phe
            60                  65                  70

TAC ACA GAG CTC AAA ACT AGG ACC AGC TCC ATC ACG CTC GCC ATA CGC       291
Tyr Thr Glu Leu Lys Thr Arg Thr Ser Ser Ile Thr Leu Ala Ile Arg
75                  80                  85                  90

ATG GAC AAC CTG TAC CTC GTG GGC TTC AGG ACC CCG GGC GGG GTG TGG       339
```

```
                Met Asp Asn Leu Tyr Leu Val Gly Phe Arg Thr Pro Gly Gly Val Trp
                                 95                  100                 105

TGG GAG TTC GGC AAG GAC GGC GAC ACC CAC CTC CTC GGC GAC AAC CCC              387
Trp Glu Phe Gly Lys Asp Gly Asp Thr His Leu Leu Gly Asp Asn Pro
        110                 115                 120

AGG TGG CTC GGC TTC GGC GGC AGG TAC CAG GAC CTC ATC GGC AAC AAG              435
Arg Trp Leu Gly Phe Gly Gly Arg Tyr Gln Asp Leu Ile Gly Asn Lys
            125                 130                 135

GGT CTG GAG ACC GTC AGC ATG GGC CGC GCC GAA ATG ACC AGG GCC GTC              483
Gly Leu Glu Thr Val Ser Met Gly Arg Ala Glu Met Thr Arg Ala Val
140                 145                 150

AAC GAC CTG GCG AAG AAG AAG GCG GCC TCC ACA CTG AAG AAG AAG                  531
Asn Asp Leu Ala Lys Lys Lys Ala Ala Ser Thr Leu Lys Lys Lys
155                 160                 165                 170

AAG GTG AAG ATG CAG ATG CAG ATG CCG AAG GCC GCT AAG CTG GCG GCG              579
Lys Val Lys Met Gln Met Gln Met Pro Lys Ala Ala Lys Leu Ala Ala
                175                 180                 185

GCT GCA GAC CCA CAG GCC GAC ACG AAG AGC AAG CTG GTG AAG CTG GTG              627
Ala Ala Asp Pro Gln Ala Asp Thr Lys Ser Lys Leu Val Lys Leu Val
            190                 195                 200

GTC ATG GTG TGC GAG GGG CTG CGG TTC AAC ACC GTG TCC CGC ACG GTG              675
Val Met Val Cys Glu Gly Leu Arg Phe Asn Thr Val Ser Arg Thr Val
        205                 210                 215

GAC GCG GGG TTC AAC AGC CAG CAC GGG GTG ACC TTG ACC GTG ACG CAG              723
Asp Ala Gly Phe Asn Ser Gln His Gly Val Thr Leu Thr Val Thr Gln
    220                 225                 230

GGG AAG CAG GTG CAG AAG TGG GAC AGG ATC TCC AAG GCG GCC TTC GAG              771
Gly Lys Gln Val Gln Lys Trp Asp Arg Ile Ser Lys Ala Ala Phe Glu
235                 240                 245                 250

TGG GCT GAC CAC CCC ACC GCT GTG ATC CCC GAC ATG CAG AAG CTT GGC              819
Trp Ala Asp His Pro Thr Ala Val Ile Pro Asp Met Gln Lys Leu Gly
                255                 260                 265

ATC AAG GAT AAG AAC GAA GCA GCG AGG ATC GTT GCG CTC GTT AAG AAT              867
Ile Lys Asp Lys Asn Glu Ala Ala Arg Ile Val Ala Leu Val Lys Asn
            270                 275                 280

CAA ACC ACC GCC GCT GCC GAC GCG TCC GCT AAG AAC AAG AAG AAG AAG              915
Gln Thr Thr Ala Ala Ala Asp Ala Ser Ala Lys Asn Lys Lys Lys Lys
        285                 290                 295

AGC ATG CCC ATT GGT GAT GAT GTC CCA ATA CTC GGG GGC ATT ATC AAT              963
Ser Met Pro Ile Gly Asp Asp Val Pro Ile Leu Gly Gly Ile Ile Asn
    300                 305                 310

GTT CAA GGC ATA AAC AGC CTT GTG TTC CAA GAT CTT GCT CGT TTT GCT             1011
Val Gln Gly Ile Asn Ser Leu Val Phe Gln Asp Leu Ala Arg Phe Ala
315                 320                 325                 330

GTT CAG GAT CAT AAT AAG AAA GAG AAG GCT CAT TTG GAG TTT GTA GAA             1059
Val Gln Asp His Asn Lys Lys Glu Lys Ala His Leu Glu Phe Val Glu
                335                 340                 345

GTT TTG AAT GTG AAG GAA CAA GTT GTT GCG GGA ATG ATG TAC TAT ATA             1107
Val Leu Asn Val Lys Glu Gln Val Val Ala Gly Met Met Tyr Tyr Ile
            350                 355                 360

ACA CTT GCG GCA ACT GAT GCT GGA AAG AAG AAA ATA TAT GAA GCT AAG             1155
Thr Leu Ala Ala Thr Asp Ala Gly Lys Lys Lys Ile Tyr Glu Ala Lys
        365                 370                 375

ATT TGG GTG AAA GAA TGG GAG GAC TTC AAG AAA GTT GTA GAG TTC AAG             1203
Ile Trp Val Lys Glu Trp Glu Asp Phe Lys Lys Val Val Glu Phe Lys
    380                 385                 390

CTT GTT GGT GAT GAT AGT GCA AAG TGATAGCTCG AGTATATA                         1245
Leu Val Gly Asp Asp Ser Ala Lys
395                 400
```

(2) INFORMATION FOR SEQ ID NO:26:

(i) SEQUENCE CHARACTERISTICS:
        (A) LENGTH: 402 amino acids
        (B) TYPE: amino acids
        (D) TOPOLOGY: linear (ii) MOLECULE TYPE: protein (xi) SEQUENCE DESCRIPTION: SEQ ID NO:26:

```
Met Ala Lys Ile Lys Leu Lys Pro Lys Lys Leu Met Ala Lys Lys Lys
1               5                   10                  15
Lys Lys Ile Val Asp Pro Lys Phe Thr Glu Ile Phe Pro Val Glu Asp
                20                  25                  30
Ala Asn Tyr Pro Tyr Ser Ala Phe Ile Ala Ser Val Arg Lys Asp Val
            35                  40                  45
Ile Lys His Cys Thr Asp His Lys Gly Ile Phe Gln Pro Val Leu Pro
50                  55                  60
Pro Glu Lys Lys Val Pro Glu Leu Trp Phe Tyr Thr Glu Leu Lys Thr
65                  70                  75                  80
Arg Thr Ser Ser Ile Thr Leu Ala Ile Arg Met Asp Asn Leu Tyr Leu
                85                  90                  95
Val Gly Phe Arg Thr Pro Gly Gly Val Trp Trp Glu Phe Gly Lys Asp
                100                 105                 110
Gly Asp Thr His Leu Leu Gly Asp Asn Pro Arg Trp Leu Gly Phe Gly
            115                 120                 125
Gly Arg Tyr Gln Asp Leu Ile Gly Asn Lys Gly Leu Glu Thr Val Ser
        130                 135                 140
Met Gly Arg Ala Glu Met Thr Arg Ala Val Asn Asp Leu Ala Lys Lys
145                 150                 155                 160
Lys Lys Ala Ala Ser Thr Leu Lys Lys Lys Val Lys Met Gln Met
                165                 170                 175
Gln Met Pro Lys Ala Ala Lys Leu Ala Ala Ala Asp Pro Gln Ala
            180                 185                 190
Asp Thr Lys Ser Lys Leu Val Lys Leu Val Met Val Cys Glu Gly
            195                 200                 205
Leu Arg Phe Asn Thr Val Ser Arg Thr Val Asp Ala Gly Phe Asn Ser
    210                 215                 220
Gln His Gly Val Thr Leu Thr Val Thr Gln Gly Lys Gln Val Gln Lys
225                 230                 235                 240
Trp Asp Arg Ile Ser Lys Ala Ala Phe Glu Trp Ala Asp His Pro Thr
                245                 250                 255
Ala Val Ile Pro Asp Met Gln Lys Leu Gly Ile Lys Asp Lys Asn Glu
            260                 265                 270
Ala Ala Arg Ile Val Ala Leu Val Lys Asn Gln Thr Thr Ala Ala Ala
        275                 280                 285
Asp Ala Ser Ala Lys Asn Lys Lys Lys Ser Met Pro Ile Gly Asp
        290                 295                 300
Asp Val Pro Ile Leu Gly Gly Ile Ile Asn Val Gln Gly Ile Asn Ser
305                 310                 315                 320
Leu Val Phe Gln Asp Leu Ala Arg Phe Ala Val Gln Asp His Asn Lys
                325                 330                 335
Lys Glu Lys Ala His Leu Glu Phe Val Glu Val Leu Asn Val Lys Glu
            340                 345                 350
Gln Val Val Ala Gly Met Met Tyr Tyr Ile Thr Leu Ala Ala Thr Asp
```

```
                355               360                 365
Ala Gly Lys Lys Ile Tyr Glu Ala Lys Ile Trp Val Lys Glu Trp
    370               375                 380

Glu Asp Phe Lys Lys Val Val Glu Phe Lys Leu Val Gly Asp Asp Ser
385               390                 395                 400

Ala Lys
```

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
GTATTGTAGA ATCAGCCATG GCAGCATAC                                29
```

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

```
GAGTACATGT AGAGCTCGTT TGATCAACA                                29
```

(2) INFORMATION FOR SEQ ID NO:29:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

```
ATG GCA GCA TAC ACC AGC AAG ATC TTT GCC CTG TTT GCC TTA ATT GCT      48
Met Ala Ala Tyr Thr Ser Lys Ile Phe Ala Leu Phe Ala Leu Ile Ala
1               5                   10                  15

CTT TCT GCA AGT GCC ACT ACT GCA ATC ACC ACT ATG CAG TAT TTC CCA      96
Leu Ser Ala Ser Ala Thr Thr Ala Ile Thr Thr Met Gln Tyr Phe Pro
            20                  25                  30

CCA ACA TTA GCC ATG GGC ACC ATG GAT CCG TGT AGG CAG TAC ATG ATG     144
Pro Thr Leu Ala Met Gly Thr Met Asp Pro Cys Arg Gln Tyr Met Met
        35                  40                  45

CAA ACG TTG GGC ATG GGT AGC TCC ACA GCC ATG TTC ATG TCG CAG CCA     192
Gln Thr Leu Gly Met Gly Ser Ser Thr Ala Met Phe Met Ser Gln Pro
    50                  55                  60

ATG GCG CTC CTG CAG CAG CAA TGT TGC ATG CAG CTA CAA GGC ATG ATG     240
Met Ala Leu Leu Gln Gln Gln Cys Cys Met Gln Leu Gln Gly Met Met
65                  70                  75                  80

CCT CAG TGC CAC TGT GGC ACC AGT TGC CAG ATG ATG CAG AGC ATG CAA     288
Pro Gln Cys His Cys Gly Thr Ser Cys Gln Met Met Gln Ser Met Gln
                85                  90                  95

CAA GTT ATT TGT GCT GGA CTC GGG CAG CAG CAG ATG ATG AAG ATG GCG     336
Gln Val Ile Cys Ala Gly Leu Gly Gln Gln Gln Met Met Lys Met Ala
```

```
ATG CAG ATG CCA TAC ATG TGC AAC ATG GCC CCT GTC AAC TTC CAA CTC        384
Met Gln Met Pro Tyr Met Cys Asn Met Ala Pro Val Asn Phe Gln Leu
        115                 120                 125

TCT TCC TGT GGT TGT TGT TGATCAAACG AGCTC                               417
Ser Ser Cys Gly Cys Cys
    130
```

(2) INFORMATION FOR SEQ ID NO:30:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

```
ATG GCA GCA TAC ACC AGC AAG ATC TTT GCC CTG TTT GCC TTA ATT GCT         48
Met Ala Ala Tyr Thr Ser Lys Ile Phe Ala Leu Phe Ala Leu Ile Ala
                 5                  10                  15

CTT TCT GCA AGT GCC ACT ACT GCA ATC ACC ACT ATG CAG TAT TTC CCA         96
Leu Ser Ala Ser Ala Thr Thr Ala Ile Thr Thr Met Gln Tyr Phe Pro
            20                  25                  30

CCA ACA TTA GCT ATG GGC ACT ATG GAT CCG TGT AGG CAG TAC ATG ATG        144
Pro Thr Leu Ala Met Gly Thr Met Asp Pro Cys Arg Gln Tyr Met Met
        35                  40                  45

CAA ACG TTG GGC ATG GGT AGC TCC ACA GCC ATG TTC ATG TCG CAG CCA        192
Gln Thr Leu Gly Met Gly Ser Ser Thr Ala Met Phe Met Ser Gln Pro
    50                  55                  60

ATG GCG CTC CTG CAG CAG CAA TGT TGC ATG CAG CTA CAA GGC ATG ATG        240
Met Ala Leu Leu Gln Gln Gln Cys Cys Met Gln Leu Gln Gly Met Met
65                  70                  75                  80

CCT CAG TGC CAC TGT GGC ACC AGT TGC CAG ATG ATG CAG AGC ATG CAA        288
Pro Gln Cys His Cys Gly Thr Ser Cys Gln Met Met Gln Ser Met Gln
                85                  90                  95

CAA GTT ATT TGT GCT GGA CTC GGG CAG CAG CAG ATG ATG AAG ATG GCG        336
Gln Val Ile Cys Ala Gly Leu Gly Gln Gln Gln Met Met Lys Met Ala
            100                 105                 110

ATG CAG ATG CCA TAC ATG TGC AAC ATG GCC CCT GTC AAC TTC CAA CTC        384
Met Gln Met Pro Tyr Met Cys Asn Met Ala Pro Val Asn Phe Gln Leu
        115                 120                 125

TCT TCC TGT GGT TGT TGT TGATCAAACG AGCTC                               417
Ser Ser Cys Gly Cys Cys
    130
```

(2) INFORMATION FOR SEQ ID NO:31:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:31:

```
Met Ala Ala Tyr Thr Ser Lys Ile Phe Ala Leu Phe Ala Leu Ile Ala
1                   5                  10                  15

Leu Ser Ala Ser Ala Thr Thr Ala Ile Thr Thr Met Gln Tyr Phe Pro
            20                  25                  30

Pro Thr Leu Ala Met Gly Thr Met Asp Pro Cys Arg Gln Tyr Met Met
        35                  40                  45
```

```
Gln Thr Leu Gly Met Gly Ser Ser Thr Ala Met Phe Met Ser Gln Pro
     50                  55                  60

Met Ala Leu Leu Gln Gln Gln Cys Cys Met Gln Leu Gln Gly Met Met
 65                  70                  75                  80

Pro Gln Cys His Cys Gly Thr Ser Cys Gln Met Met Gln Ser Met Gln
             85                  90                  95

Gln Val Ile Cys Ala Gly Leu Gly Gln Gln Met Met Lys Met Ala
            100                 105                 110

Met Gln Met Pro Tyr Met Cys Asn Met Ala Pro Val Asn Phe Gln Leu
        115                 120                 125

Ser Ser Cys Gly Cys Cys
    130
```

(2) INFORMATION FOR SEQ ID NO:32:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

```
CATGATCACC ACTATGCAGT ATTTCCCACC AACATTAGCT ATGGGCACTA TG          52
```

(2) INFORMATION FOR SEQ ID NO:33:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

```
GATCCATAGT GCCCATAGCT AATGTTGGTG GGAAATACTG CATAGTGGTG AT          52
```

(2) INFORMATION FOR SEQ ID NO:34:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

```
ATG ATC ACC ACT ATG CAG TAT TTC CCA CCA ACA TTA GCT ATG GGC ACT      48
Met Ile Thr Thr Met Gln Tyr Phe Pro Pro Thr Leu Ala Met Gly Thr
 1               5                  10                  15

ATG GAT CCG TGT AGG CAG TAC ATG ATG CAA ACG TTG GGC ATG GGT AGC      96
Met Asp Pro Cys Arg Gln Tyr Met Met Gln Thr Leu Gly Met Gly Ser
            20                  25                  30

TCC ACA GCC ATG TTC ATG TCG CAG CCA ATG GCG CTC CTG CAG CAG CAA     144
Ser Thr Ala Met Phe Met Ser Gln Pro Met Ala Leu Leu Gln Gln Gln
        35                  40                  45

TGT TGC ATG CAG CTA CAA GGC ATG ATG CCT CAG TGC CAC TGT GGC ACC     192
Cys Cys Met Gln Leu Gln Gly Met Met Pro Gln Cys His Cys Gly Thr
    50                  55                  60

AGT TGC CAG ATG ATG CAG AGC ATG CAA CAA GTT ATT TGT GCT GGA CTC     240
```

```
Ser Cys Gln Met Met Gln Ser Met Gln Val Ile Cys Ala Gly Leu
 65                  70                  75                  80

GGG CAG CAG CAG ATG ATG AAG ATG GCG ATG CAG ATG CCA TAC ATG TGC    288
Gly Gln Gln Gln Met Met Lys Met Ala Met Gln Met Pro Tyr Met Cys
                 85                  90                  95

AAC ATG GCC CCT GTC AAC TTC CAA CTC TCT TCC TGT GGT TGT TGT        333
Asn Met Ala Pro Val Asn Phe Gln Leu Ser Ser Cys Gly Cys Cys
                100                 105                 110

TGATCAAACG AGCTC                                                   348

(2) INFORMATION FOR SEQ ID NO:35:

(i) SEQUENCE CHARACTERISTICS:
        (A) LENGTH: 111 amino acids
        (B) TYPE:  amino acid
        (D) TOPOLOGY:  linear (ii) MOLECULE TYPE:  protein (xi) SEQUENCE DESCRIPTION:  SEQ ID NO:35:

Met Ile Thr Thr Met Gln Tyr Phe Pro Pro Thr Leu Ala Met Gly Thr
 1               5                  10                  15

Met Asp Pro Cys Arg Gln Tyr Met Met Gln Thr Leu Gly Met Gly Ser
                20                  25                  30

Ser Thr Ala Met Phe Met Ser Gln Pro Met Ala Leu Leu Gln Gln Gln
             35                  40                  45

Cys Cys Met Gln Leu Gln Gly Met Met Pro Gln Cys His Cys Gly Thr
 50                  55                  60

Ser Cys Gln Met Met Gln Ser Met Gln Gln Val Ile Cys Ala Gly Leu
 65                  70                  75                  80

Gly Gln Gln Gln Met Met Lys Met Ala Met Gln Met Pro Tyr Met Cys
                 85                  90                  95

Asn Met Ala Pro Val Asn Phe Gln Leu Ser Ser Cys Gly Cys Cys
                100                 105                 110

(2) INFORMATION FOR SEQ ID NO:36:

(i) SEQUENCE CHARACTERISTICS:
        (A) LENGTH:  533 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:36:

CAG GAC CTC ATC GGC AAC AAG GGT CTG GAG ACC GTC AGC ATG GGC CGC    48
Gln Asp Leu Ile Gly Asn Lys Gly Leu Glu Thr Val Ser Met Gly Arg
 1               5                  10                  15

GCC GAA ATG ACC AGG GCC GTC AAC GAC CTG GCG AAG AAG AAG AAG GCG    96
Ala Glu Met Thr Arg Ala Val Asn Asp Leu Ala Lys Lys Lys Lys Ala
                20                  25                  30

GCG GCC GCC ACA CTG AAG AAG AAG AAG GTG AAG ATG CAG ATG CAG ATG    144
Ala Ala Ala Thr Leu Lys Lys Lys Lys Val Lys Met Gln Met Gln Met
             35                  40                  45

CCG AAG GCC GCT AAG CTG GCG GCG GCT GCA GAC CCA CAG GCC GAC ACG    192
Pro Lys Ala Ala Lys Leu Ala Ala Ala Ala Asp Pro Gln Ala Asp Thr
 50                  55                  60

AAG AGC AAG CTG GTG AAG CTG GTG GTC ATG GTG TGC GAG GGG CTG CGG    240
Lys Ser Lys Leu Val Lys Leu Val Val Met Val Cys Glu Gly Leu Arg
 65                  70                  75                  80
```

-continued

```
TTC AAC ACC GTG TCC CGC ACG GTG GAC GCG GGG TTC AAC AGC CAG CAC         288
Phe Asn Thr Val Ser Arg Thr Val Asp Ala Gly Phe Asn Ser Gln His
                85                  90                  95

GGG GTG ACC TTG ACC GTG ACG CAG GGG AAG CAG GTG CAG AAG TGG GAC         336
Gly Val Thr Leu Thr Val Thr Gln Gly Lys Gln Val Gln Lys Trp Asp
        100                 105                 110

AGG ATC TCC AAG GCG GCC TTC GAG TGG GCT GAC CAC CCC ACC GCT GTG         384
Arg Ile Ser Lys Ala Ala Phe Glu Trp Ala Asp His Pro Thr Ala Val
            115                 120                 125

ATC CCC GAC ATG CAG AAG CTT GGC ATC AAG GAT AAG AAC GAA GCA GCG         432
Ile Pro Asp Met Gln Lys Leu Gly Ile Lys Asp Lys Asn Glu Ala Ala
    130                 135                 140

AGG ATC GTT GCG CTC GTT AAG AAT CAA ACC ACC GCC GCT GCC GAC GCG         480
Arg Ile Val Ala Leu Val Lys Asn Gln Thr Thr Ala Ala Ala Asp Ala
145                 150                 155                 160

TCC GCT AAG AAC AAG AAG AAG AGC ATG CCC GCC TAGTAGCTCG                  526
Ser Ala Lys Asn Lys Lys Lys Ser Met Pro Ala
                165                 170

AGTATAT                                                                 533

(2) INFORMATION FOR SEQ ID NO:37:

(i) SEQUENCE CHARACTERISTICS:
        (A) LENGTH: 3496 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

ATG GCA ATC GTA GGA GGC CTT GTC GAT GTT CCA TTC GAA AAC AAA GTC         48
Met Ala Ile Val Gly Gly Leu Val Asp Val Pro Phe Glu Asn Lys Val
1               5                   10                  15

GAG TTT GAT GAT CTT GCT CGT TTT GCT GTC CAA GAT TAC AAT CAG AAA         96
Glu Phe Asp Asp Leu Ala Arg Phe Ala Val Gln Asp Tyr Asn Gln Lys
                20                  25                  30

AAT GTAAAGAATT ATTTTTCATT TACTTCGATT ACATCTTAGC TTTGTTATGA              149
Asn

AAAGTTACAT GTCTTAGTTA ACATAATTGA TAGTGTAAAA TATCTACACA TCATCCGTGC       209

ACAACATTTA AAATGCATTA ATGTTACAAA TAAGCAGATG ACTCTTCGAA GAATATATAA       269

TTAATTTTGA AATGCTTAAT TACTTTGTGA ATAATTAGTT GATTCAGATG ACTATTCATA       329

TTTGTTTCAT TTCAACAACA TATATTTTGT ATTTCAGGAT TCT AGT TTG GAG TTT         384
                                            Ser Ser Leu Glu Phe
                                                        35

AAA AAG GTT TTG AAC GTG AAG CAA CAA ATA GTT GCT GGA ATA ATG TAC         432
Lys Lys Val Leu Asn Val Lys Gln Gln Ile Val Ala Gly Ile Met Tyr
        40                  45                  50

TAC ATA ACA TTT GAG GCA ACT GAA GGT GGA AAC AAG AAA GAA TAT GAA         480
Tyr Ile Thr Phe Glu Ala Thr Glu Gly Gly Asn Lys Lys Glu Tyr Glu
55                  60                  65                  70

GCC AAG ATT TTG CTG AGG AAA TGG GAG GAC TTG AAG AAA GTT GTA GGA         528
Ala Lys Ile Leu Leu Arg Lys Trp Glu Asp Leu Lys Lys Val Val Gly
                75                  80                  85

TTC AAG CTT GTT GGT GAT GAT AGT ACA ATG CCT GGG GGC ATT GTC AAT         576
Phe Lys Leu Val Gly Asp Asp Ser Thr Met Pro Gly Gly Ile Val Asn
                90                  95                  100

GTT CCA AAC CCA AAC AAC ACC AAG TTT CAA GAA CTT GCT CGT TTT GCT         624
Val Pro Asn Pro Asn Asn Thr Lys Phe Gln Glu Leu Ala Arg Phe Ala
            105                 110                 115
```

```
ATT CAG GAT TAT AAT AAA AAA CAG GTTAATTATA ATTACTTACT CCTCTTTTAT      678
Ile Gln Asp Tyr Asn Lys Lys Gln
    120                 125

TTTTTCGTTA ATTTCATATT TAAATCCCGA TTTCACTATA GTAGTACCAA CATCATACAC     738

AATCTATTTT CCAG AAT GCT CAT TTG GAG TTT GTA GAA AAT TTG AAT GTT      788
            Asn Ala His Leu Glu Phe Val Glu Asn Leu Asn Val
                        130                 135

AAA GAG CAA GTT GTT GCT GGA ATC ATG TAC TAT ATA ACA CTT GCG GCA      836
Lys Glu Gln Val Val Ala Gly Ile Met Tyr Tyr Ile Thr Leu Ala Ala
    140                 145                 150

ACT GAT GAT GCT GGA AAG AAG AAA ATA TAC AAA GCT AAG ATT TGG GTG      884
Thr Asp Asp Ala Gly Lys Lys Lys Ile Tyr Lys Ala Lys Ile Trp Val
155                 160                 165                 170

AAG GAA TGG GAG GAC TTC AAG AAA GTT GTA GAA TTC AAG CTT GTT GGT      932
Lys Glu Trp Glu Asp Phe Lys Lys Val Val Glu Phe Lys Leu Val Gly
                175                 180                 185

GAT GAT ATT GCA AAA CTT GGG GGC ATT ACT GAT GTT CCA TTC CCA AAT      980
Asp Asp Ile Ala Lys Leu Gly Gly Ile Thr Asp Val Pro Phe Pro Asn
            190                 195                 200

AAC CCC GAG TTC CAA GAT CTT GCT CGT TTT GCT ATT CAA GTT TAT AAT     1028
Asn Pro Glu Phe Gln Asp Leu Ala Arg Phe Ala Ile Gln Val Tyr Asn
        205                 210                 215

AAG AAA GAG GTTAATTCAA ATGGCTTACT CTCCTCTTTT ATTTTTCGCT             1077
Lys Lys Glu
        220

AGTTTCACCT TCAAACTTAT AATATTTTCT GAATCCTCCG CTACAGTTTC TAATAATTCT    1137

TTCATTTGAA TGAATGCCAT ATACAATCTA TTTTTCA AAT GTT CAT TTG GAG TTT    1192
                                     Asn Val His Leu Glu Phe
                                                         225

GTA GAA AAT TTG AAC GTT AAA CAG CAA GTT GTT GCT GGA ATG ATG TAC     1240
Val Glu Asn Leu Asn Val Lys Gln Gln Val Val Ala Gly Met Met Tyr
                230                 235                 240

TAT ATA ACA CTT GCG GCA ATT GAT GCT GGA AAG AAG AAA ATA TAT GAA     1288
Tyr Ile Thr Leu Ala Ala Ile Asp Ala Gly Lys Lys Lys Ile Tyr Glu
        245                 250                 255

ACT AAG ATT TGG GTG AAG GAA TGG GAG GAC TTC AAG AAA GTT GTA GAA     1336
Thr Lys Ile Trp Val Lys Glu Trp Glu Asp Phe Lys Lys Val Val Glu
260                 265                 270                 275

TTC AAG CTT GTT GGT GAT GAT AGT GCA AAA ACT GGG GGC ATT ATC AAT     1384
Phe Lys Leu Val Gly Asp Asp Ser Ala Lys Thr Gly Gly Ile Ile Asn
                280                 285                 290

GTT CCA AAC CCA AAC AGC CCC GAG TTC CAA GAT CTT GCT CGT TTT GCT     1432
Val Pro Asn Pro Asn Ser Pro Glu Phe Gln Asp Leu Ala Arg Phe Ala
            295                 300                 305

GTT CAG GAT TAT AAT AAT ACA CAG GTCAATTATA TAATGACT TACTTTTAGT      1486
Val Gln Asp Tyr Asn Asn Thr Gln
        310                 315

TTCTTCTTTT TTTGTTAATT TCACATTAAA ACCTATAATA TTCAAATCTT TAATCTATTG   1546

CAGTATCTAA TAATACTTTC ATTTGAACAA ATGTCATATA CAATCTACTT TTCAG AAT    1604
                                                             Asn

GCT CAT TTG GAG TTT GTA GAA AAT TTG AAT GTG AAA GAA CAA CTT GTT     1652
Ala His Leu Glu Phe Val Glu Asn Leu Asn Val Lys Glu Gln Leu Val
        320                 325                 330

TCT GGA ATG ATG TAC TAT ATA ACA CTT GCG GCA ACT GAT GCC GGG AAT     1700
Ser Gly Met Met Tyr Tyr Ile Thr Leu Ala Ala Thr Asp Ala Gly Asn
            335                 340                 345

AAG AAA GAA TAT GAA GCC AAG ATT TGG GTG AAG GAA TGG GAG GAC TTC     1748
```

```
                                                               -continued

Lys Lys Glu Tyr Glu Ala Lys Ile Trp Val Lys Glu Trp Asp Phe
    350                 355                 360

AAG AAA GTT ATA GAC TTC AAG CTT GTT GGT AAT GAT AGT GCG AAA AAA    1796
Lys Lys Val Ile Asp Phe Lys Leu Val Gly Asn Asp Ser Ala Lys Lys
365                 370                 375                 380

CTT GGG GGC TTT ACC GAA GTT CCA TTC CCA AAC AGC CCC GAG TTT CAA    1844
Leu Gly Gly Phe Thr Glu Val Pro Phe Pro Asn Ser Pro Glu Phe Gln
                    385                 390                 395

GAT CTT ACA CGT TTT GCT GTT CAC CAA TAT AAT AAG GAC CAG            1886
Asp Leu Thr Arg Phe Ala Val His Gln Tyr Asn Lys Asp Gln
            400                 405                 410

GTTATTTATA ATGACTTGCT CATCTTCTAT TTTTTTTTTC TAGTTAATTT CACATTCAAC  1946

CCTATAATAT TCAAATTCAT AATCCACTAC TGTATCTAGT ATATAATTCT TTCATTTGAA  2006

CGAGTGTCAT ATACAATCAA TTTTTTCAG AAT GCT CAT CTG GAG TTT GTA GAA    2059
                                Asn Ala His Leu Glu Phe Val Glu
                                                        415

AAT TTG AAT GTG AAA AAA CAA GTT GTT GCT GGA ATG TTG TAC TAC ATA    2107
Asn Leu Asn Val Lys Lys Gln Val Val Ala Gly Met Leu Tyr Tyr Ile
    420                 425                 430

ACA TTT GCG GCA ACA GAT GGT GGA AAG AAA AAA ATA TAT GAA ACT AAG    2155
Thr Phe Ala Ala Thr Asp Gly Gly Lys Lys Lys Ile Tyr Glu Thr Lys
435                 440                 445                 450

ATT TGG GTT AAG GTA TGG GAG AAC TTC AAG AAA GTT GTT GAA TTC AAG    2203
Ile Trp Val Lys Val Trp Glu Asn Phe Lys Lys Val Val Glu Phe Lys
                    455                 460                 465

CTT GTT GGT GAT GAT AGT GCA AAG CTT GGG GGC ATT ATC AAT GTT CCA    2251
Leu Val Gly Asp Asp Ser Ala Lys Leu Gly Gly Ile Ile Asn Val Pro
            470                 475                 480

TTC CCA AAC AAC CCC GAA TTC CAA GAT CTT GCT CGT TTT GCT GTT CAA    2299
Phe Pro Asn Asn Pro Glu Phe Gln Asp Leu Ala Arg Phe Ala Val Gln
                485                 490                 495

GAT TAT AAT AAG AAA GAG GTTAATTAAA ATGACTTACT CCTTCTTAAT           2347
Asp Tyr Asn Lys Lys Glu
            500

TTTTTCGTTA GTTTCACATT TCAAATCTAT AATATTCAAA TCCAGATATT CCACTACATT  2407

ATCTAATAAT ACTTTCATTT GAACGAATTT CATATACAAT CTACTTTTCA G AAT GCT   2464
                                                         Asn Ala
                                                         505

CAT TTG GAG TTT GTA GAA AAT TTG AAT GTG AAA GAA CAA CTT GTT GCT    2512
His Leu Glu Phe Val Glu Asn Leu Asn Val Lys Glu Gln Leu Val Ala
            510                 515                 520

GGA ATG TTA TAC TAC ATA ACA CTT GTG GCA ATT GAT GCT GGA AAG AAA    2560
Gly Met Leu Tyr Tyr Ile Thr Leu Val Ala Ile Asp Ala Gly Lys Lys
        525                 530                 535

AAA ATA TAT GAA GCT AAG ATT TGG GTT AAG GAA TGG GAG AAC TTC AAG    2608
Lys Ile Tyr Glu Ala Lys Ile Trp Val Lys Glu Trp Glu Asn Phe Lys
540                 545                 550

AAA GTT ATT GAA TTC AAA CTT ATT GGT GAT GAT AGT GGC TTT ACT GAT    2656
Lys Val Ile Glu Phe Lys Leu Ile Gly Asp Asp Ser Gly Phe Thr Asp
    555                 560                 565                 570

GTT CCA TTC CCA AAC AAC CCC GAG TTC CAA GAC CTT GCA ATA ATT GGG    2704
Val Pro Phe Pro Asn Asn Pro Glu Phe Gln Asp Leu Ala Ile Ile Gly
                575                 580                 585

GCT CGT TTT GCT GTT CAG GAT TAT AAC AAG AAA GAG GTTATTATAA         2750
Ala Arg Phe Ala Val Gln Asp Tyr Asn Lys Lys Glu
            590                 595

TGAATTACTC ATCTTTTATT TTATTCTCGT TAATTTCACA TTCAAACCTA TAATATTCAA  2810
```

```
ATCCATAATC CACTACATTA TCTAATAATT ATTTCATTTG AATGAACGTC ATATACAATC        2870

TATTTTTCAG AAT GCT CAC TTG GAG TAT GTA GAA AAT TTG AAT GTG AAA          2919
           Asn Ala His Leu Glu Tyr Val Glu Asn Leu Asn Val Lys
               600             605             610

GAG CAA CTT GTT GCT GGA ATG ATA TAC TAT ATA ACA CTT GTG GCA ACT         2967
Glu Gln Leu Val Ala Gly Met Ile Tyr Tyr Ile Thr Leu Val Ala Thr
            615             620             625

GAT GCT GGA AAA AAG AAA ATA TAT GAA GCT AAG ATT TGG GTG AAG GAA         3015
Asp Ala Gly Lys Lys Lys Ile Tyr Glu Ala Lys Ile Trp Val Lys Glu
            630             635             640

TGG GAG GAC TTC AAA AAA GTT GTA GAA TTC AAG CTT GTT GGT GAT GAT         3063
Trp Glu Asp Phe Lys Lys Val Val Glu Phe Lys Leu Val Gly Asp Asp
            645             650             655

AGT GCA AAA CCT GGG GGC ATT ATC ATT GTT CCA TTC CCA AAC AGT CCT         3111
Ser Ala Lys Pro Gly Gly Ile Ile Ile Val Pro Phe Pro Asn Ser Pro
660             665             670             675

GAG TTC CAA GAT CTT GCT CGT TTT GCT GTT CAA GAT TTT AAT AAG AAA         3159
Glu Phe Gln Asp Leu Ala Arg Phe Ala Val Gln Asp Phe Asn Lys Lys
            680             685             690

GAG GTTAATTCCC TAAATTAAAA TGACTTAATC TTCTTTTATC TTCCGTTAGT              3212
Glu

TTCATATTCA AATTTATACT ATTTAAATCC TGAATTTACT GTTGTATCGA ATAATTCTTT       3272

TATTTGAACG AACGTCGTAT GCTCTATTTC AG AAT GGT CAT TTG GAG TTT GTA        3325
                                   Asn Gly His Leu Glu Phe Val
                                               695

GAA AAT TTG AAT GTG AAG GAA CAA GTT GTT GCT GGA ATG ATG TAC TAT         3373
Glu Asn Leu Asn Val Lys Glu Gln Val Val Ala Gly Met Met Tyr Tyr
700             705             710             715

ATA ACA CTT GCG GCA ACT GAT GCT AGA AAG AAG GAA ATA TAT GAG ACC         3421
Ile Thr Leu Ala Ala Thr Asp Ala Arg Lys Lys Glu Ile Tyr Glu Thr
            720             725             730

AAA ATT TTG GTG AAG GAA TGG GAG AAT TTC AAG GAA GTT CAA GAA TTC         3469
Lys Ile Leu Val Lys Glu Trp Glu Asn Phe Lys Glu Val Gln Glu Phe
            735             740             745

AAG CTT GTT GGT GAT GCT ACA AAG TGA                                     3496
Lys Leu Val Gly Asp Ala Thr Lys
            750             755

(2) INFORMATION FOR SEQ ID NO:38:

(i) SEQUENCE CHARACTERISTICS:
        (A) LENGTH:  755 amino acids
        (B) TYPE:  amino acid
        (D) TOPOLOGY:  linear (ii) MOLECULE TYPE:  protein (xi) SEQUENCE DESCRIPTION:  SEQ ID NO:38:

Met Ala Ile Val Gly Gly Leu Val Asp Val Pro Phe Glu Asn Lys Val
1               5                   10                  15

Glu Phe Asp Asp Leu Ala Arg Phe Ala Val Gln Asp Tyr Asn Gln Lys
                20                  25                  30

Asn Ser Ser Leu Glu Phe Lys Lys Val Leu Asn Val Lys Gln Gln Ile
            35                  40                  45

Val Ala Gly Ile Met Tyr Tyr Ile Thr Phe Glu Ala Thr Glu Gly Gly
        50                  55                  60

Asn Lys Lys Glu Tyr Glu Ala Lys Ile Leu Leu Arg Lys Trp Glu Asp
65              70                  75                  80

Leu Lys Lys Val Val Gly Phe Lys Leu Val Gly Asp Asp Ser Thr Met
```

-continued

```
                    85                  90                  95
Pro Gly Gly Ile Val Asn Val Pro Asn Pro Asn Asn Thr Lys Phe Gln
                100                 105                 110

Glu Leu Ala Arg Phe Ala Ile Gln Asp Tyr Asn Lys Lys Gln Asn Ala
            115                 120                 125

His Leu Glu Phe Val Glu Asn Leu Asn Val Lys Glu Gln Val Val Ala
        130                 135                 140

Gly Ile Met Tyr Tyr Ile Thr Leu Ala Ala Thr Asp Ala Gly Lys
145                 150                 155                 160

Lys Lys Ile Tyr Lys Ala Lys Ile Trp Val Lys Glu Trp Glu Asp Phe
                165                 170                 175

Lys Lys Val Val Glu Phe Lys Leu Val Gly Asp Asp Ile Ala Lys Leu
            180                 185                 190

Gly Gly Ile Thr Asp Val Pro Phe Pro Asn Asn Pro Glu Phe Gln Asp
        195                 200                 205

Leu Ala Arg Phe Ala Ile Gln Val Tyr Asn Lys Lys Glu Asn Val His
    210                 215                 220

Leu Glu Phe Val Glu Asn Leu Asn Val Lys Gln Gln Val Val Ala Gly
225                 230                 235                 240

Met Met Tyr Tyr Ile Thr Leu Ala Ala Ile Asp Ala Gly Lys Lys Lys
                245                 250                 255

Ile Tyr Glu Thr Lys Ile Trp Val Lys Glu Trp Glu Asp Phe Lys Lys
            260                 265                 270

Val Val Glu Phe Lys Leu Val Gly Asp Asp Ser Ala Lys Thr Gly Gly
        275                 280                 285

Ile Ile Asn Val Pro Asn Pro Asn Ser Pro Glu Phe Gln Asp Leu Ala
    290                 295                 300

Arg Phe Ala Val Gln Asp Tyr Asn Asn Thr Gln Asn Ala His Leu Glu
305                 310                 315                 320

Phe Val Glu Asn Leu Asn Val Lys Glu Gln Leu Val Ser Gly Met Met
                325                 330                 335

Tyr Tyr Ile Thr Leu Ala Ala Thr Asp Ala Gly Asn Lys Lys Glu Tyr
            340                 345                 350

Glu Ala Lys Ile Trp Val Lys Glu Trp Glu Asp Phe Lys Lys Val Ile
        355                 360                 365

Asp Phe Lys Leu Val Gly Asn Asp Ser Ala Lys Lys Leu Gly Gly Phe
    370                 375                 380

Thr Glu Val Pro Phe Pro Asn Ser Pro Glu Phe Gln Asp Leu Thr Arg
385                 390                 395                 400

Phe Ala Val His Gln Tyr Asn Lys Asp Gln Asn Ala His Leu Glu Phe
                405                 410                 415

Val Glu Asn Leu Asn Val Lys Lys Gln Val Val Ala Gly Met Leu Tyr
            420                 425                 430

Tyr Ile Thr Phe Ala Ala Thr Asp Gly Gly Lys Lys Ile Tyr Glu
        435                 440                 445

Thr Lys Ile Trp Val Lys Val Trp Glu Asn Phe Lys Val Val Glu
    450                 455                 460

Phe Lys Leu Val Gly Asp Asp Ser Ala Lys Leu Gly Gly Ile Ile Asn
465                 470                 475                 480

Val Pro Phe Pro Asn Asn Pro Glu Phe Gln Asp Leu Ala Arg Phe Ala
                485                 490                 495

Val Gln Asp Tyr Asn Lys Lys Glu Asn Ala His Leu Glu Phe Val Glu
            500                 505                 510
```

```
Asn Leu Asn Val Lys Glu Gln Leu Val Ala Gly Met Leu Tyr Tyr Ile
        515                 520                 525

Thr Leu Val Ala Ile Asp Ala Gly Lys Lys Ile Tyr Glu Ala Lys
    530                 535                 540

Ile Trp Val Lys Glu Trp Glu Asn Phe Lys Lys Val Ile Glu Phe Lys
545                 550                 555                 560

Leu Ile Gly Asp Asp Ser Gly Phe Thr Asp Val Pro Phe Pro Asn Asn
                565                 570                 575

Pro Glu Phe Gln Asp Leu Ala Ile Ile Gly Ala Arg Phe Ala Val Gln
            580                 585                 590

Asp Tyr Asn Lys Lys Glu Asn Ala His Leu Glu Tyr Val Glu Asn Leu
        595                 600                 605

Asn Val Lys Glu Gln Leu Val Ala Gly Met Ile Tyr Tyr Ile Thr Leu
        610                 615                 620

Val Ala Thr Asp Ala Gly Lys Lys Ile Tyr Glu Ala Lys Ile Trp
625                 630                 635                 640

Val Lys Glu Trp Glu Asp Phe Lys Lys Val Glu Phe Lys Leu Val
                645                 650                 655

Gly Asp Asp Ser Ala Lys Pro Gly Gly Ile Ile Ile Val Pro Phe Pro
                660                 665                 670

Asn Ser Pro Glu Phe Gln Asp Leu Ala Arg Phe Ala Val Gln Asp Phe
            675                 680                 685

Asn Lys Lys Glu Asn Gly His Leu Glu Phe Val Glu Asn Leu Asn Val
        690                 695                 700

Lys Glu Gln Val Val Ala Gly Met Met Tyr Tyr Ile Thr Leu Ala Ala
705                 710                 715                 720

Thr Asp Ala Arg Lys Lys Glu Ile Tyr Glu Thr Lys Ile Leu Val Lys
                725                 730                 735

Glu Trp Glu Asn Phe Lys Glu Val Gln Glu Phe Lys Leu Val Gly Asp
                740                 745                 750

Ala Thr Lys
        755

(2) INFORMATION FOR SEQ ID NO:39:

(i) SEQUENCE CHARACTERISTICS:
        (A) LENGTH:   24 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:39:

TACACCAGCA AGATCTTTGC CCTG                                              24

(2) INFORMATION FOR SEQ ID NO:40:

(i) SEQUENCE CHARACTERISTICS:
        (A) LENGTH:   27 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:40:

CTGCCTACAC GGATCCATAG TGCCCAT                                           27
```

NUCLEOTIDE SEQUENCES OF GENES ENCODING SINK PROTEIN AND USES THEREOF FOR IMPROVING THE NUTRITIONAL QUALITY OF FEEDS

REFERENCE TO RELATED APPLICATIONS

This application claims the benefit of U.S. Provisional Application No. 60/052,552 filed Jul. 15, 1997.

FIELD OF INVENTION

The present invention relates to the preparation and use of genes encoding various sink proteins and the use thereof to improve the nutritional quality of animal feeds.

BACKGROUND OF THE INVENTION

Each year, over 2.5 billion bushels of corn seed are processed as animal feeds (hereinafter feed(s)) for cattle, poultry, swine, and the like. This single use accounts for approximately 35% of the total United States corn production. However, corn seed is not an optimal feed source due to the low abundance of essential amino acids such as methionine, tryptophan, lysine and the like. Low abundance of these amino acids in corn seed is thought to be due to the absence of appropriate "sink proteins" which act as reservoirs for said amino acids. Therefore, current use of corn for feeds requires the addition of supplements obtained from other sources, such as soybeans or purified amino acids, to address these deficiencies and thus prevent stunted animal growth and development.

The term "sink protein" is frequently associated with the term "storage protein" albeit there are differences between the two. Storage proteins are thought to fulfill a role as a nitrogen reservoir within cells; a pool in which a variety of different amino acids can be deposited for future use. These proteins can then be proteolyzed at a later time, such as germination, to provide the amino acids necessary for proper cell growth and development. Amino acids found in storage proteins are typically used directly for incorporation into other proteins or used as substrates in the biosynthesis of additional amino acids or other metabolites [Staswick (1990) The Plant Cell, (1990) 2:1–6.]. Many examples of storage proteins are noted in the art including the beta-conglycinins found in soybean seed, and patatin, the major storage protein found in potato tubers.

Sink proteins, often found in large abundance, differ from storage proteins in that they contain a higher than the averaged amount of one or more specific amino acids. They are usually classified by their most abundant amino acid and are thought to serve as stable reservoirs for such. The sulfur-rich sink proteins, those being rich in cysteine and methionine, and their corresponding genes have been studied most thus far. These include a 15 kDa zein-class sink protein for corn [Pedersen et al., (1986) J. Biol. Chem. 261:6279–6284]; a 10 kDa zein-class sink protein from corn [Kirihara et al., (1988) Gene 71:359–370]; two genes from pea seed encoding albumins [Higgins et al., (1986) J. Biol. Chem. 261:11124–11130]; and a gene from Brazil nut encoding a seed 2S albumin [Altenbach et al., (1987) Plant Mol. Biol. 8:239–250].

Evidence presented in the art to date suggests that biosynthesis rates of amino acids in plants do not vary substantially when compared one to another. However, the final averaged amino acid content of a seed by dry weight can vary dramatically depending on the plant species. In some cases, variations observed in final amino acid content are related to the tolerance of the cell to free amino acid levels (those not incorporated into protein). Tolerance levels of said free amino acids are most often maintained and regulated through feedback mechanisms involving enzymes that are sensitive to the size of free amino acid pools. In addition, free amino acids may be degraded. For example, the enzyme lysine-ketoglutarate reductase monitors and degrades free lysine in corn endosperm thereby preventing its accumulation to levels that may disrupt cell metabolism [Arruda and Silva, (1982) Eur. J. Biochem. 209:933–937; Brochetta-Braga et al., (1992) Plant Physiol. 98:1139–1147]. However, if amino acids are incorporated into protein, they are removed from the "free" pool and thus prevented from exceeding tolerance limits. Incorporation into protein also prevents limitations placed on biosynthesis rates through biochemical feedback mechanisms.

The low abundance of certain amino acids accumulated in a cell by dry weight can also be correlated to the low abundance of certain amino acids in specific sink or storage proteins. For example, while seeds may not need high levels of certain amino acids to maintain their physiological viability, these low levels result in the feeds derived thereof to be nutritionally unbalanced. Low levels of tryptophan, cysteine and methionine in corn kernels may be traced directly to the nominal frequency of these amino acid in zeins, the major storage protein in corn kernels. Although there may be other proteins in corn kernels having higher levels of tryptophan, cysteine, and methionine, accumulated levels of these proteins are not high enough to result in a substantial contribution to the total amino acid profile. Increased expression of proteins which can act as sink proteins or introduction of new sink proteins in a seed can improve the total amino acid profile.

Currently, nutritional deficiencies in feeds are augmented by supplementation with soybean meal and/or the purified amino acids of interest. However, this results in overall higher feed cost due to the cost associated with supplements as well as increased handling and processing requirements. Therefore, it would be quite desirous for feeds to be obtained from genetically engineered seeds endogenously expressing sink proteins that would improve the nutritional balance of said feed. It would also be desirous for the sink proteins used as amino acid supplements to improve the nutritional balance of feeds to be produced less expensively through the use of molecular biology and heterologous expression systems. The inventions, as described herein, address these problems and therefore will allow small farm owners/operators to produce nutritionally balanced feeds at reduced cost.

SUMMARY OF THE INVENTION

In the present invention, genes encoding storage proteins have been isolated, cloned and modified to encode sink proteins. Furthermore, genes encoding naturally occurring sink proteins have been isolated and cloned. Said genes can be expressed in cells to produce proteins. These expressed proteins can be added to feeds to improve the nutritional value thereof.

One aspect of the disclosed invention is the development of methods whereby genes encoding storage proteins can be modified to encode sink proteins. More specifically, the modified genes encode Tryptophan sink protein (hereinafter TSP), which has been created from bark storage protein (hereinafter BSP) by genetically performing conservative substitutions of tryptophan for specific phenylalanine residues. The addition of TSP to feeds can improve the tryptophan content therein and the nutritional value thereof. Another aspect of the present invention relates to methods for increasing the specific amino acid content of proteins having naturally occurring proteolytically processed regions. Specifically, the genes encoding proteolytically processed regions are modified to encode peptides wherein conservative substitutions are made. More specifically, the modified genes encode for lysine enriched ribosome inactivating protein (KRIP) and derivatives thereof. Expressing genes encoding for KRIP and derivatives thereof can produce proteins which can improve the nutritional balance of feeds.

Another aspect of the present inventions relates to methods of creating a single gene encoding for two or more individual sink proteins being linked together. More specifically, the genes encode for RIP-5, containing a derivative of KRIP and a sub-domain of potato multicystatin (PMC). Different sink proteins covalently linked together can improve the nutritional value of feeds by increasing the levels of either the same or different amino acids.

Another aspect of the present invention relates to isolating and cloning gene fragments encoding naturally occurring sink proteins. More specifically, the isolated genes encode potato multicystatin and sub-domains thereof (hereinafter PMC) and the 10 kDa rice prolamin protein (hereinafter RP-10). Expressing said genes can increase the nutritional value of feeds by producing PMC and RP-10, proteins naturally rich in lysine and methionine, respectively.

An additional aspect of the present invention is the production of a chimeric gene using the genes and nucleic acid fragments disclosed herein in combination with promoter regulatory elements and the use of said chimeric genes within a cell.

A further aspect of the present invention is the transformation of a cell with genes encoding sink proteins, said cells being of either eukaryotic or prokaryotic origin.

Yet an additional aspect of the present invention is the transformation of plants with said chimeric genes.

Other aspects, embodiments, advantages, and features of the present invention will become apparent from the following specification.

DETAILED DESCRIPTION OF THE INVENTION

The present invention relates to methods and compositions for obtaining animal feeds with improved nutritional value. The following phrases and terms are defined below:

By "chimeric DNA construction" is meant a recombinant DNA containing genes or portions thereof from one or more species.

By "conservative substitution" is meant the changing of one amino acid for another as defined herein.

By "developmental specific" promoter is meant promoter elements responsible for gene expression at specific plant developmental stages, such as in early or late embryogenesis.

By added "endogenously" is meant a heterologous gene encoding a protein expressed within a plant seed, said seed being the main component of feed, by improving the nutritional balance thereof. The genes can be introduced by standard transformation methods.

By "enhancer" is meant nucleotide sequence elements which can stimulate promoter activity such as those from maize streak virus (MSV) and alcohol dehydrogenase intron 1.

By added "exogenously" is meant a protein that is added as a supplement to feed to improve the nutritional balance thereof. The protein can be obtained from its natural source or from a heterologous gene expressed in a heterologous system, such as bacteria, yeast, insect cells, plants, and the like. The protein is then added to feed as a nutritional supplement.

By "expression", as used herein, is meant the transcription and stable accumulation of the mRNA and/or protein with a cell. Expression of genes involves transcription of DNA into RNA, processing of the RNA into mRNA in eukaryotic systems, translation of mRNA into precursor and mature proteins, followed by, in some cases, post-translational modifications. It is not necessary that the DNA integrate into the genome of the cell in order to achieve expression. This definition in no way limits expression to a particular system and is meant to include all types including cellular, transient, in vitro, in vivo, and viral expression systems in both prokaryotic and eukaryotic cells.

By "heterologous gene" is meant a gene encoding a protein whose exact amino acid sequence is not normally found in the host cell, but is introduced by standard gene transfer techniques.

By "linking peptide" is meant the amino acids being used to covalently attach two or more protein subunits together. The number of amino acids making up the linking peptide is no less than one and is typically no greater than thirty-six.

By "linked protein" is meant two or more protein subunits covalently linked to each upon translation by a linking peptide. Upon complete protein folding, the two protein subunits may or may not remain linked.

By "gene" is meant to include all genetic material involved in protein expression within prokaryotic or eukaryotic cells including chimeric DNA constructions, genes, plant genes and plant optimized genes.

By "genome" is meant genetic material contained in each cell of an organism and/or a virus.

By "heterologous system" is meant an expression system into which a heterologous gene is introduced and therefore used to produce the sink protein of interest. Examples include but are not limited to yeast, plants, bacteria and the like.

By "inducible promoter" is meant promoter elements causing gene transcription in response to a specific signal such as a chemical, physical stimulus, light, hormone, and stress.

By "mole percent" is meant the number of a particular amino acid residues found in a particular protein divided by the total number of amino acid residues found in that protein. For example, a protein having 10 lysine residues out of 100 total amino acids would be 10 mole percent lysine.

By "nutritional supplement" is meant a material that is added to feed to increase the nutritional value beyond that observed in the absence thereof. Nutritional supplements can be added either endogenously or exogenously.

By "oligonucleotides" it is meant a molecule consisting of a short chain of nucleotides of either RNA or DNA. Such length could be at least one nucleotide, but typically are in the range of about 10 to about 30 nucleotides. Oligonucleotides may be less than 10 or greater than 30.

By "peptide" it is meant a molecule consisting of a short chain of amino acids. Such length is at least one amino acid, but typically are in the range of between about 2 to about 34 amino acids.

By "plant" is meant a photosynthetic organism, either eukaryotic or prokaryotic.

By "plant gene" is meant a gene encoded by a plant.

By "plant optimized gene" is meant a heterologous gene designed for plant expression.

By "promoter regulatory element" is meant nucleotide sequence elements within a nucleic acid fragment or gene which control the expression of that gene. Promoter regulatory elements from a variety of sources can be used efficiently in plant cells to express gene constructs. Promoter regulatory elements are meant to include constitutive, tissue-specific, developmental-specific, inducible promoters and the like. Promoter regulatory elements may also include certain enhancer sequence elements that improve transcriptional efficiency. Promoter regulatory sequence elements are recognized by RNA polymerase and other transcription factors required for efficient transcription.

By "sink proteins" and "amino acid sink proteins" is meant a protein that contains a higher than averaged abundance of one or more specific amino acids. Sink proteins can be identified by examining the primary amino acid sequence and determining the mole percent of specific amino acids as defined herein. Sink proteins for use in corn should have mole percent levels, as defined herein, of lysine, methionine, and tryptophan greater than about 5.30, about 2.34 and about 1.39 percent, respectively. Sink proteins may or may not accumulate to levels greater than about 1% by dry weight within its native cell. In addition, sink proteins can occur naturally or be can created.

By "storage protein" is meant a protein that does not contain a higher than averaged abundance of one or more specific amino acids. In corn, storage proteins have mole percent levels of lysine, methionine, and tryptophan less than about 5.30, about 2.34 and about 1.39 percent, respectively. Storage proteins typically accumulate to levels greater than about 1% by dry weight within its native cell.

By "sub-domain" is meant a portion of protein that has function in and of itself. Said function can include enzymatic activity and the ability of the protein to withstand proteolytic degradation. For example, potato multicystatin contains 8 distinct sub-domains.

By "tissue-specific promoter" is meant promoter elements responsible for gene expression at a specific plant developmental stage, such as in early or late embryogenesis, or only in a specific plant cell type, such as meristem, phloem, and the like.

By "transgenic plant" is meant a plant expressing a foreign or heterologous gene.

Corn seed, in combination with other grains and supplements, is widely used as a feed source for animals. In unaltered form, the seed contains on average about 71.3% starch, about 9.9% protein and about 4.45% fat [Glover and Mertz, in Nutritional Quality of Cereal Grains: Genetic and Agronomic Improvement (1987) Olson and Frey, Eds. American Society of Agronomy, Inc. 183–336]. Although highly digestible, the proteins that comprise standard hybrid corn seed have natural levels of lysine, tryptophan, and methionine that are well below the amount needed for proper animal growth and development (Table 1). This requires that feed made from corn be supplemented with additional amounts of lysine tryptophan and methionine.

Supplementation results in higher feed prices due to the increased cost associated with processing and supplements. Typically, the levels of amino acids are tested with the ground corn and the exact amount of amino acids needed to nutritionally balance the feed is determined. Therefore, producing seed having increased endogenous levels of lysine, tryptophan, and/or methionine at any amount beyond what is found naturally in unaltered seed is desirable because it will lower the amount of amino acids needed and subsequently, the cost thereof. Also desirable are proteins which can be easily expressed in heterologous systems such as bacteria, baculovirus and the like.

TABLE 1

Nutritional Value of Corn as a Source of Animal Feed[a,b]

| Amino Acid | Amount in Corn Kernels*[a] | Amount Needed** |
|---|---|---|
| Lysine | 0.25 | 0.85 |
| Tryptophan | 0.09 | 0.15 |
| Methionine | 0.18 | 0.60 |

[a]Dale, N. (1996) Feedstuffs Reference Issue 68:24–31.
[b]Levels of individual lines, hybrids and samples may vary.
*Amino acid level by dry weight (g Amino Acid/100 g seed).
**Amount of amino acid by dry weight needed to produce nutritionally balanced feed (g Amino Acid/100 g Kernels).

Said proteins can then be added as a cost-effective supplement to improve the nutritional value of feed.

As described herein, the nutritional value of feeds can be increased by adding, either endogenously or exogenously, naturally occurring sink proteins or sink proteins created by modifying storage proteins as disclosed herein. Preferably, proteins and genes thereof used as described herein are distinguished as having one or more of the following characteristics: (i) being of plant, bacterial or fungal origin; (ii) accumulating at levels up to about 50% by dry weight of the total protein in its native species; (iii) having about 1 mole percent or greater the amino acid of interest or having about 1 mole percent or greater amino acids capable of conservative substitutions; and (iv) being generally accepted as safe for animal consumption.

Also preferred are genes encoding proteins containing peptides regions that are proteolytically processed-upon translation. The gene fragments encoding said proteolytically processed peptides can then be modified to create genes encoding peptides enriched for specific amino acids.

More preferred are naturally occurring sink proteins and modified storage proteins creating sink proteins that can added to improve the nutritional value of feeds. Most preferred are sink proteins having from about 1.4 to about 3.4 mole percent tryptophan, sink proteins having from about 5.3 to about 14.9 mole percent lysine, and/or sink proteins having from about 2.35 to about 17.2 mole percent methionine. Most preferred are also those sequences disclosed herein as SEQ ID NO:1, SEQ ID NO:2, SEQ ID NO:5, SEQ ID NO:6, SEQ ID NO:9, SEQ ID NO:10, SEQ ID NO:13, SEQ ID NO:14, SEQ ID NO:16, SEQ ID NO:17, SEQ ID NO:20, SEQ ID NO:21, SEQ ID NO:22, SEQ ID NO:23, SEQ ID NO:25, SEQ ID NO:26, SEQ ID NO:29, SEQ ID NO:30, SEQ ID NO:31, SEQ ID NO:34, SEQ ID NO:35, SEQ ID NO:37, and SEQ ID NO:38 and the use thereof to improve the nutritional value of feeds.

Storage proteins identified from plant, bacterial, and fungal sources are preferred for modifying into sink proteins. This is due to their ability to often accumulate to levels reaching 50% by dry weight of the total protein within the cell [Coleman et. al., (1991) Plant Physiol. 96:686–692; Clausen and Apel, (1991) Plant Mol. Biol. 17:669–678; Galliard, (1971) J. Biochem. 121:379–390; Racusen and Foote, (1980) J. Food Biochem. 13:453–456]. Studies of proteins encoded by gene families have revealed several amino acids which are naturally replaced with others without effecting protein stability. Therefore, sink proteins can be created from storage proteins by performing conservative substitutions of one amino acid for another. The "conservative substitutions" preferred include replacement of arginine or serine with lysine, as well as the substitution of leucine, isoleucine, and valine with methionine [Johnson and Overington (1993) J. Mol. Biol. 233:716–738]. Most preferred is the conservative substitution of phenylalanine and tyrosine residues with tryptophan.

Conservative substitutions are most favored on the protein's surface because disruption of a protein's core structure can create cavities within its hydrophobic center, thus leading to instability (Eriksson et al., (1992) Science, 255:178–183]. Identification of amino acids located on the protein's surface can most easily be determined by examining the placement of charged amino acids. Since removal of charged amino acids interacting with water can negatively affect protein stability, most proteins naturally fold in a manner that places charged amino acids on the protein's surface [Schulz and Schirmer in Principles of Protein Structure. New York, N.Y., Springer-Verlag, 1979]. Therefore, only the amino acids described herein that are adjacent in primary sequence to charged amino acids are considered capable of conservative substitution.

A storage protein can be enriched for tryptophan by examining the primary sequence of said protein to identify phenylalanine residues next to the charged or polar amino acids selected from the group consisting of aspartic acid, glutamic acid, arginine, tyrosine, serine, asparagine, lysine, glutamine, and threonine. Phenylalanine residues so identified are candidates for conservative substitutions with tryptophan. A gene encoding a protein wherein conservative substitutions have been made can be created using standard molecular biology techniques and said gene can be expressed as described herein. Addition of this protein can improve the nutritional balance of feeds.

When performing conservative substitutions of bark storage protein (hereinafter BSP) [Coleman et. al., (1991) Plant Physiol. 96:686–692; Clausen and Apel, (1991) Plant Mol. Biol. 17:669–678] using the methods described herein, is it most desirable to create a protein having 3.4 mole percent tryptophan, as seen with tryptophan sink protein (hereinafter TSP) (SEQ ID NO:1). This protein can be used to increase the tryptophan content of feeds from about 0.09% by dry weight up to about 0.15% by dry weight.

Sink proteins can be modified to increase the nutritional value of feeds by modifying regions within said proteins that are proteolytically processed upon mRNA translation. Processed regions can be modified in content by conservative substitution of amino acids selected from the group consisting of serine, threonine, asparagine, glutamine, tyrosine, cysteine, lysine, arginine, histidine, aspartic acid, glutamic acid, asparagine, and glutamine with lysine. The high frequency of these selected amino acids proteolyzed regions in proteins is consistent with the regions being on the protein surface. Processed regions can be easily identified by comparison of a protein's amino-terminal sequence to the protein sequence determined by gene cloning methods. Other methods used to determine proteolytic processed site can be found in Colligan et al., Current Protocols in Protein Science. Chanda, V. B, Ed. (1997) John Wiley & Sons, Inc., which is incorporated herein by reference.

When performing conservative substitutions of proteolyzed regions in modified maize ribosome inactivating protein (RIPΔNIC; described previously in U.S. Pat. Nos. 5,248,606 and 5,635,384 to DowElanco and incorporated herein by reference) using the methods described herein, it is most desirable to create a protein having up to about 14.4 mole percent lysine, as seen with KRIP (SEQ ID NO:25) and derivatives thereof having the sequence according to SEQ ID NO:5; SEQ ID NO:9; SEQ ID NO:13; and SEQ ID NO:16. This protein can be used to increase the lysine content of feeds from about 0.25% by dry weight up to about 0.85% by dry weight.

A single gene can be designed wherein it encodes two separate proteins covalently linked together through linking peptides. Genes encoding proteins attached by linking peptides can be produced using techniques familiar to one of ordinary skill in the art of molecular biology. The first and second proteins linked through a linking peptide can be characterized as having at least one of the following: accumulating to levels equal to or greater than 1% by dry weight in their native species and having 1 mole percent or greater the amino acid of interest or amino acids capable of conservative substitutions. The proteins linked together can be either identical or different; however, they are encoded by a single gene when linked together. In addition, proteins covalently linked together can address the either the same or different nutritional deficiency.

When linking proteins together through a linking peptide, it is most desirable that one protein be a sub-domain of PMC, wherein that sub-domain is covalently attached by a linking peptide to a derivative of RIPΔNIC as described herein to create RIP-5 (SEQ ID NO:22). Linking of the two proteins results in creation of RIP-5, having up to 14.4 mole percent lysine. The protein encoded by this gene (SEQ ID NO:22) can be used to increase the lysine content of feeds from about 0.25% by dry weight up to about 0.85% by dry weight.

The nutritional value of feeds can be increased by expressing genes encoding naturally occurring sink proteins isolated from other sources. Genes encoding those sink proteins, selected based on the criteria described herein, can be isolated using techniques as further described herein. Once the genes have been isolated, said proteins can be expressed, either endogenously or exogenously, and added to feed to provide higher than normal levels of lysine, methionine and/or tryptophan by dry weight.

It is most desirable to use PMC (SEQ ID NO:37) when increasing the lysine content of feed with a sink protein isolated from other sources. This protein can added to feeds thereby increasing the lysine content therein from about 0.25 to about 0.85% by dry weight.

It is also most desirable to use RP-10 (SEQ ID NO:30 and SEQ ID NO:31) when increasing the methionine content of feed with sink proteins isolated from other sources. This protein can be added to feeds thereby increasing the methionine content therein from about 0.18 to about 0.6% by dry weight.

The production of sink proteins in a cell requires nucleic acid sequences encoding amino acid sequences for the sink protein of interest. The nucleic acid sequence is then integrated into a protein expression vector appropriate to the host in which the vector will be expressed.

There are many ways available to one skilled in the art to obtain nucleic acid sequences encoding sink protein or storage protein candidates that can be designed and modified into sink proteins. One such way is to isolate the native genetic material which produces the sink protein using information deduced from the protein's amino acid sequence. Using N-terminal amino acid sequence data, one can construct oligonucleotides complementary to all, or a section of, the DNA bases that encode the amino acids of the protein of interest. These oligonucleotides can be labeled using techniques familiar to one skilled in the art and used as molecular probes to isolate the genetic material from a genomic library built from genetic material of the source from which the protein is found.

Screening a genetic library using oligonucleotides requires the production of a battery of oligonucleotides, since the degenerate genetic code allows an amino acid to be encoded in the DNA by any of several three-nucleotide combinations. For example, the amino acid arginine can be encoded by nucleic acid triplets CGA, CGC, CGG, CGT, AGA, and AGG. Since one cannot predict which triplet is used at those positions in the gene encoding the protein, one must prepare oligonucleotides with each potential triplet represented. The genetic library can be cloned in plasmid, cosmid, phage or phagemid vectors. The library can then be transformed into *Escherichia coli*. Additionally, the transformed bacterial cells can be screened for protein production using antibodies raised against the protein of interest.

From the amino acid sequence of the purified protein, genetic materials responsible for the production of the protein can readily be isolated and cloned, in whole or in part, into an expression vector using any of several techniques well-known to one skilled in the art of molecular biology. A typical expression vector is a DNA plasmid, though other transfer means including, but not limited to, cosmids, phagemids and bacteriophage are also envisioned. In addition to features required or desired for plasmid replication, such as an origin of replication and antibiotic resistance or another form of a selectable marker such as the bar gene of *Streptomyces hygroscopicus* or *viridochromogenes*, protein expression vectors normally additionally require an expression cassette which incorporates the cis-acting sequences necessary for transcription and translation of the gene of interest. The cis-acting sequences required for expression in prokaryotes differ from those required in eukaryotes and therefore plants.

An eukaryotic expression cassette requires a transcriptional promoter upstream (5') to the gene of interest, a transcriptional termination region such as a poly-A addition site, and a ribosome binding site upstream of the gene of interest's first codon. In bacterial cells, a useful transcriptional promoter that could be included in the vector is the T7 RNA Polymerase-binding promoter. Promoters, as included herein, are known to efficiently promote transcription of mRNA. Upstream from the gene of interest the vector may also include a nucleotide sequence encoding a signal sequence known to direct a covalently linked protein to a particular compartment of the host cell, such as the cell surface, endoplasmic reticulum, organelle or vacuole.

To obtain high expression of heterologous genes in plants it is preferred to reengineer said genes so that they are more efficiently expressed in the cytoplasm of plant cells. Maize is one such plant where it is preferred to reengineer the heterologous gene(s) prior to transformation to increase the expression level in the plant. Therefore, an additional step in the design of genes encoding sink proteins is the designed reengineering of the heterologous gene for optimal expression.

One reason for the reengineering of genes encoding sink proteins for expression in maize is the non-optimal G+C content of many non-maize genes. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of the gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding sink proteins for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding sink proteins is to generate a DNA sequence in which the sequence modifications do not hinder translation.

The table below illustrates how high the G+C content is in maize. For the data in Table 2, coding regions of the genes were extracted from GenBank (Release 71) entries, and base compositions were calculated using the MacVector™ program (IBI, New Haven, Conn.). Intron sequences were ignored in the calculations.

Due to the plasticity afforded by the redundancy of the genetic code (i.e., some amino acids are specified by more than one codon), evolution of the genomes of different organisms or

TABLE 2

Compilation of G + C contents of protein coding regions of maize genes.

| Protein Class[a] | Range % G + C | Mean % G + C[b] |
|---|---|---|
| Metabolic Enzymes (76) | 44.4–75.3 | 59.0 (8.0) |
| Structural Proteins (18) | 48.6–70.5 | 63.6 (6.7) |
| Regulatory Proteins (5) | 57.2–68.9 | 62.0 (4.9) |
| Uncharacterized Proteins (9) | 41.5–70.3 | 64.3 (7.2) |
| All Proteins (108) | 44.4–75.3 | 60.8 (5.2) |

[a]Number of genes in class given in parentheses.
[b]Standard deviations given in parentheses.
[c]Combined groups mean ignored in mean calculation.

classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In reengineering genes encoding sink protein for maize expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined as well as the second and third choice of preferred codons. The amino acid sequence of the sink protein of interest is reverse translated so that the resulting nucleic acid sequence codes for the same protein as the native gene wanting to be heterologously expressed. The new DNA sequence is designed using the information regarding codon bias so that it corresponds to the most preferred codons of the desired plant. The new sequence is analyzed for restriction enzyme sites that might have been created by the modification. The identified sites are further modified by replacing the codons with second or third choice with preferred codons. Other sites in the sequence which could affect transcription or translation of the gene of interest are the exon:intron 5' or 3' junctions, poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

It is preferred that the plant optimized gene(s) encoding sink proteins contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3.

TABLE 3

Preferred amino acid codons for proteins expressed in maize.

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

The method described above enables one skilled in the art to modify gene(s) that are foreign to a particular plant so that the genes are optimally expressed in plants. The method is further illustrated in pending application U.S. Ser. No. 60/005,405 filed on Oct. 13, 1995, which is incorporated herein by reference. In order to design plant optimized genes encoding sink proteins, the amino acid sequence of the sink proteins are reverse translated into a DNA sequence utilizing a non-redundant genetic code assembled from a codon bias table compiled for the gene sequences for the particular plant, as shown in Table 3. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

In another aspect of the invention, genes encoding sink proteins are expressed from transcription units inserted into the plant genome. Preferably, the recombinant vectors capable of stable integration into the plant genome and selection of transformed plant lines expressing the sink proteins are expressed either by constitutive or inducible promoters in the plant cell. Once expressed, the mRNA is translated into sink proteins, thereby incorporating amino acids of interest into protein. The genes encoding sink proteins expressed in the plant cells are under the control of a constitutive promoter, a tissue-specific promoter or an inducible promoter.

It is theorized that genes encoding sink proteins that have been derived from bacterial sources may be more easily expressed in plants if said genes are expressed in plastids. Thus, it may be possible to express bacterial genes encoding sink proteins in plants, without optimizing the genes for plant expression, and obtain high expression of the protein. Furthermore, it may also be possible to design a plant gene encoding a sink protein having a bacterial codon bias such that it could express more efficiently in plant plastids (See U.S. Pat. Nos. 4,762,785; 5,451,513 and 5,545,817, which are incorporated herein by reference).

Incorporation of genetic material that encodes sink proteins into the genome of a plant would allow production of seeds or kernels expressing said proteins thereby supplementing nutritional deficiencies found currently in feeds from unprocessed seed stocks. Achieving endogenous expression would include transformation of the host of interest with the expression vector containing the gene encoding the sink protein. Numerous members of the monocotyledonous and dicotyledenous genera have been transformed. Transgenic agronomic important crops are of commercial interest. Such crops include but are not limited to maize, rice, soybeans, canola, sunflower, alfalfa, sorghum, wheat, cotton, peanuts, tomatoes, potatoes, and the like.

Several techniques exist for introducing foreign genetic material into plant cell, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco). Plants may be transformed using Agrobacterium technology, see U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149, 645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302, 523 and 5,464,765 both to Zeneca. Electroporation technology has also been used to transform plants, see WO 87/06614 to Boyce Thompson Institute, U.S. Pat. Nos. 5,472,869 and 5,384,253 both to Dekalb, WO9209696 and WO9321335 both to Plant Genetic Systems. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques described herein.

Another variable is the choice of a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorosulfuron; bromoxynil, dalapon and the like.

In addition to a selectable marker, it may be desirous to use a reporter gene. In some instances a reporter gene may be used without a selectable marker. Reporter genes are genes which are typically not present or expressed in the recipient organism or tissue. The reporter gene typically encodes for a protein which provides for some phenotypic change or enzymatic property. Examples of such genes are provided in K. Weising et al. Ann. Rev. Genetics, 22, 421 (1988), which is incorporated herein by reference. A preferred reporter gene is the beta-glucuronidase (GUS) gene.

Regardless of transformation technique, the gene encoding a sink protein is preferably incorporated into a gene transfer vector adapted to express the sink protein in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S) and the like may be used. Plant promoters include, but are not limited to ribulose-1,6-bisphosphate (RUBP) carboxylase small subunit (ssu), beta-conglycinin promoter, phaseolin promoter, ADH promoter, heat-shock promoters and tissue specific promoters. Promoters may also contain certain enhancer sequence elements that may improve the transcription efficiency. Typical enhancers include but are not limited to Adh-intron 1 and Adh-intron 6. Constitutive promoters may also be used.

Constitutive promoters direct continuous gene expression in all cells types and at all times (e.g., actin, ubiquitin, CaMV 35S). Tissue specific promoters are responsible for gene expression in specific cell or tissue types, such as the leaves or seeds (e.g., zein, oleosin, napin, ACP, globulin and the like) and these promoters may also be used. Promoters may also be active during a certain stage of the plants' development as well as active in plant tissues and organs. Examples of such promoters include but are not limited to pollen-specific, embryo specific, corn silk specific, cotton fiber specific, root specific, seed endosperm specific promoters and the like.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used. Numerous plant-specific gene transfer vectors are known to the art. Insect viruses, or baculoviruses, are known to infect insect cells and produce large quantities of protein, therefore, it may be possible to ferment sink proteins in large quantities for exogenous supplementation. A particularly useful vector for sink protein genes is the nuclear polyhedrosis virus. Transfer vectors using this virus have been described and are now the vectors of choice for transferring foreign genes into insects and insect cell culture. The sink protein gene may also be inserted behind a strong viral coat protein.

Sink proteins may be produced as a secreted or cellular protein originally expressed in a heterologous prokaryotic or eukaryotic host. Bacteria are typically the hosts in which heterologous proteins are expressed, as described herein. Eukaryotic hosts could include but are not limited to plants, insect cells, and yeast. Upon expression, these sink proteins can then be added exogenously to the feed as a nutritional supplement.

In addition to genes encoding sink proteins, the scope of the present invention is intended to include related nucleic acid sequences which encode amino acid biopolymers homologous to the sink proteins described herein, thereby increasing the nutritional value of feeds.

Other envisioned modifications of the nucleic acid include the addition of targeting sequences to direct the sink proteins to particular parts of the plant cell for improving its accumulation.

In some cases, it may be desirable purify, either partially or completely, the sink protein of interest before added to feeds. Typically, the expression in bacteria or other cells leads high concentrations of proteins. These cells can then be harvested most effectively by centrifugation. Following the cells can be lysed, as described herein, and purified using commercially available chromatography techniques. Details of various protein purification procedures can be found in Colligan et al., Current Protocols in Protein Science. Chanda, V. B, Ed. (1997) John Wiley & Sons, Inc., which is incorporated herein by reference. In other cases, it might be desirable to add the proteins without harvesting and purifying.

The particular embodiments of this invention are further exemplified in the Examples. However, those skilled in the art will readily appreciate that the specific experiments detailed are only illustrative of the invention as described more fully in the claims which follow thereafter.

EXAMPLE 1

Design and Synthesis of a Gene Encoding a Tryptophan-enriched Sink Protein

Standard methods of DNA purification, restriction enzyme digestion, agarose gel analysis, DNA fragment isolation, ligation and transformation were used as described in Sambrook et al., (Molecular Cloning a Laboratory Manual, $2^{nd}$ edition, New York, Cold Spring Harbor Laboratory Press, 1989; Ausubel et al., Eds. Current Protocols in Molecular Biology. New York, John Wiley and Sons, 1987). Enzymes used for genetic manipulations were from either Pharmacia LKB Biotechnology (Piscataway, N.J.), Bethesda Research Labs (Gaithersburg, Md.) or New England Biolabs (Beverly, Mass.). Buffers and protocols used for enzyme reactions were provided by the manufacturer. All genetic manipulations were done in E. coli strain DH5-α from Bethesda Research Labs.

Oligonucleotide primers were synthesized on an Applied Biosystems Model 394 DNA/RNA Synthesizer (Foster City, Calif.). Following synthesis the primers were suspended in 100–300 µL of TE [1 mM Tris-HCl, 1 mM ethylenediaaminetetraacetic acid (EDTA), pH 7.5] and the concentration was determined using absorbance at 260 nm. Oligonucleotides were then purified on polyacrylamide gels. Gels were cast in a Hoefer Sturdier apparatus (Pharmacia Biotech, Piscataway, N.J.) using 16×18 cm plates, 2 mm thick spacers and a five tooth comb (2 cm/tooth). The gel consisted of either 9 or 12% polyacrylamide (20:1 polyacrylamide:bis) in 1×TBE [0.09 M Tris base, 0.09 M boric acid, 0.002 M EDTA, pH 8.0] having 7 M urea. The gel was polymerized by adding 350 µL of 10% (w/v) ammonium persulfate and 30 µL N,N,N',N'-tetramethylethylenediamine (TEMED) per 50 mL gel mix. TBE buffer (1×) was used as running buffer. The resuspended primers were mixed with an equal volume of sequence gel loading buffer [98% deionized formamide, 0.5×TBE, bromphenol blue and xylene cyanol], heated to 90–100° C. for 5 min and cooled on ice. Two hundred µg of DNA were loaded per lane. Gels were run at 250 V for 3 hr or until the bromphenol blue tracking dye reached the bottom of the gel. The gel was then transferred to a sheet of plastic wrap and placed on a Cronex™ $P^{32}$ intensifying screen (DuPont, Wilmington, Del.). UV-shadowing of oligonucleotides was performed using a hand held UV lamp at 254 nm. The highest molecular weight band was then excised from the gel and prepared for elution.

DNA was eluted from the excised gel by cutting the gel slice into 1–2 mm pieces, placing it into 2 mL of elution buffer [0.1 M Tris pH 8.0, 0.5 M NaCl, 0.005 M EDTA] and incubating at 65° C. for 1–2 hr with periodic vortexing. Oligonucleotides were purified from elution buffer using Sep-Pak™ C18 cartridge chromatography (Waters Inc., Milford, Mass.). The column was activated with 60% methanol followed by washing with deionized water. After the elution buffer mixture was loaded, the column was washed with 10 mL of deionized water. Oligonucleotides were then eluted with 3 mL of 60% methanol and dried under vacuum. Purified oligonucleotides were then suspended in 100 µL of TE.

A Perkin-Elmer Cetus Thermocycler (Norwalk, Conn.) was used for all polymerase chain reaction (hereinafter PCR) amplifications. The reaction (50 µL total volume) contained ca. 100 ng of template DNA and 35 pmol of each primer in 10 mM Tris-HCl pH 8.3, 50 mM KCl, 1.5 mM $MgCl_2$, 0.001% gelatin, 0.2 mM deoxyribonucleotide triphosphates (dNTP) and 1.25 units of Taq DNA polymerase (Boerhinger Mannheim, Indianapolis, Ind.). Template DNAs were taken from previous reactions as described below, isolated on TAE [0.04M Tris-acetate pH 8.0, 0.001 M EDTA] agarose gels (1–1.5%), and purified using Qiaex™ (Qiagen Inc., Chatsworth, Calif.) according to the manufacturer's instructions. Gene synthesis cycle parameters were as follows: 15 cycles of [94° C. for 1 min; 50° C. for 2 min; and 72° C. for 3 min] followed by 72° C. for 7 min.

DNA sequences were obtained using an Applied Biosystems 373A DNA Sequencer (Foster City, Calif.). Template DNA was double stranded plasmid suspended in water. Oligonucleotide primers were also suspended in water at 0.8 pmol/µL. Reactions (20 µL total volume) consisted of 1.5 µg template DNA, 4 µL primer, 1 µL dimethylsulfoxide (DMSO), 9.5 µL PRISM™ mix (Applied Biosystems). Thermocycler conditions were as follows: 25 cycles of [96° C. for 15 sec; 50° C. for 15 sec; 60° C. for 4 min]. The reaction mixture was purified using a Centra-Sep™ column (Princeton Separations, Adelphia, N.J.) according to manufacturer's instructions, dried under vacuum and analyzed.

Tryptophan storage protein (hereinafter TSP) was created by designing a gene wherein codons encoding specific phenylalanine residues within the bark storage protein (hereinafter BSP) from *Populus deltoides* [Clausen and Apel, (1991) Plant Mol. Biol. 17:669–678] were modified to encode for tryptophan. Identification of specific phenylalanine residues designated for codon replacement was determined by examining the primary sequence of BSP for phenylalanine residues that were adjacent in sequence to charged amino acids. This allowed the identification of eight phenylalanine residues located at positions 64, 97, 138, 150, 228, 238, 243 and 300 relative to the amino terminus of the BSP protein. The DNA sequence of BSP was then modified so that all eight codons encoding for phenylalanine were changed to encode for tryptophan therefore creating TSP.

The gene encoding TSP (SEQ ID NO:1) was engineered to direct the protein, having the amino acid sequence according to SEQ ID NO:2, to the vacuolar compartment of endosperm cells. Vacuolar targeting required two signals, an amino-terminal signal sequence which directed the polypeptide to the endoplasmic reticulum and a carboxy-terminal vacuolar signal [Chrispeels, (1991) Annu. Rev. Plant. Physiol. 42:21–53; Chrispeels and Raikhel (1992) Cell, 68: 613–616]. An endoplasmic reticulum signal sequence selected from zein 22.1 [Garratt et al., (1993) Proteins: Structure, Function, and Genetics 15:88–99] was used to replace the 25 amino-terminal amino acids of BSP. The barley lectin vacuolar signal sequence was added to the carboxy terminus [Dombrowski et al., (1993) The Plant Cell 5:587–596]. The amino acid sequences for these signals and the TSP gene were reverse translated and adjusted to reflect the maize codon bias as disclosed herein (Table 3). These sequences were added in the last round of PCR mediated gene synthesis as described below.

The entire TSP gene (SEQ ID NO:1) was synthesized de novo which allowed conversion of the eight phenylalanine codons to tryptophan, the incorporation of unique restriction sites, and the utilization of maize codon bias. The first step in this process was the reverse translation of the TSP amino acid sequence (SEQ ID NO:2) to a DNA sequence. This primary DNA sequence was then adjusted to represent the codon bias for maize as shown in Table 3. During the adjustment process the DNA sequence was continuously monitored for a series of unfavorable expression sequences. These sequences included intron:exon junctions, polyadenylation signals, RNA polymerase termination signals, TA and CG doublets as well as inconvenient restriction sites as described in Brown, (1986) Nucl. Acids Res. 14:9549–9559; Joshi, (1987) Nucl. Acids.Res. 15:9627–9640; Vankan and Filipowicz, (1988) EMBO J. 7:791–799; Boudraa and Perrin, (1988) Nucl. Acids Res. 15:5729–5737; and Ohno and Yomo, (1990) Proc. Natl. Acad. Sci. USA 87:1218–1222 and incorporated herein by reference. Codon selection was modified to eliminate these unfavorable sequences from the gene.

Once the TSP sequence was suitably adjusted to reflect a maize codon bias and all possible unfavorable sequences were eliminated, strategic restriction sites were designed into the gene. The derived amino acid sequence of TSP was scanned for specific amino acid pairs which could result in six base cutter restriction sites. The codons were then adjusted, considering the maize codon bias (Table 3), to create unique restriction sites. Unique sites were designed into the sequence every 200–300 base pairs (bp).

The designed TSP gene (SEQ ID NO:1) was synthesized using the PCR methods and parameters described herein. Synthesis began in the center of the gene with two primers which overlapped. The second PCR reaction used product from the first reaction as template; however, the second set of primers overlapped the template by ca. 20 base pairs and extended for an additional 60 base pairs. This process was continued for a total of 9 primer sets. Primers were approximately 80 base pairs in length with a 20 base pair overlap. This resulted in the creation of a DNA molecule having a sequence according to SEQ ID NO:1 and encoding a protein having an amino acid sequence according to SEQ ID NO:2.

EXAMPLE 2

Design and Construction of a High Lysine Storage Protein Gene

Standard methods of DNA purification, restriction enzyme digestion, agarose gel analysis, DNA fragment isolation, ligation and transformation were used as described above. Following restriction digestion, overhanging ends were in some cases treated with T4 DNA polymerase to create blunt ends. Typically, 5 μg of plasmid containing the DNA of interest were restricted, extracted with 25:24:1 (v/v) phenol:chloroform:isoamyl alcohol and precipitated with ethanol. The DNA was then suspended in 10 μL of TE and treated with 3 units of T4 DNA polymerase (Boehringer Mannheim) in a total volume of 25 μL in 1× T4 buffer (provided by the manufacturer) containing 200 mM dNTP. The reaction was incubated at 37° C. for 30 min followed by recovery of the treated DNA by phenol extraction and ethanol precipitation. Double stranded DNA oligonucleotide segments were prepared as follows: 50 pmol of each single stranded complementary oligonucleotide were mixed in 25 μL of 1× One-for-All™ buffer (Pharmacia, Piscataway N.J.). The DNA was treated with 10 units T4 Polynucleotide kinase (Pharmacia, Piscataway N.J.) at 37° C. for 30 min. The sample was then overlaid with a drop of mineral oil and incubated at 65° C. for 20 min to kill the kinase activity. The oligonucleotides were annealed by allowing the samples to cool to room temperature. The sample was used directly for ligation into plasmids. Expression of heterologous genes in *E. coli* was done using the T7 polymerase system as described in Studier et al., (1990) Methods Enzymol., 185:60–839.

The backbone of the high lysine ribosome inactivating protein (hereinafter KRIP) was an extensively engineered derivative of ribosome inactivating protein, hereinafter RIPΔNIC, as previously described (Hey et al., (1995) Plant Physiol. 107:1323–1332). A 25 amino acid lysine insertion into pro-RIP was the first lysine-enriched segment to be added thereby creating RIP-2. The carboxy terminal segment was the second lysine-enriched segment to be added thereby creating RIP-4. Following the addition of a protease inhibitor domain to the 3' end of the gene as a lysine rich sub-domain (RIP-5), the amino terminal segment was replaced to create KRIP.

TABLE 4

Names and modifications to various RIP genes.

| Gene | Modification to RIPDNIC | DNA SEQ ID NO: |
|---|---|---|
| RIP-1 | Insertion of unique NotI and PstI in center | SEQ ID NO:5 |
| RIP-2 | Insertion of lysine region into RIP-1 | SEQ ID NO:9 |
| RIP-3 | Removal of Nco I site in RIP-2 center | SEQ ID NO:13 |
| RIP-4 | Addition of lysine region at 3' end of RIP-3 | SEQ ID NO:16 |

TABLE 4-continued

Names and modifications to various RIP genes.

| Gene | Modification to RIPDNIC | DNA SEQ ID NO: |
|---|---|---|
| RIP-5 | Addition of PMC sub-domain to 3' end of RIP-4 | SEQ ID NO:22 |
| KRIP | Addition of lysine region 5' to RIP-5 | SEQ ID NO:25 |

In each case the processed segment was modified to include strategic restriction sites as well as substitutions of lysine for charged and polar amino acids within the segment coding region. Since the engineering required several steps, each derivative leading to KRIP was named as shown in Table 4.

The first step in creating KRIP was to replace the interdomain insertion of maize RIP with a lysine-rich insertion. To introduce the modified insertion sequence, unique restriction sites were engineered into RIPΔNIC at the natural insertion site corresponding to lysine 161 and threonine 284 of the proRIP sequence as described by Hey et al., (1995), Plant Physiol. 107:1323–1332. The restriction sites were chosen based on the most compatible amino acids encoded by the recognition sequence. NotI and PstI sites were subsequently engineered into the insertion site. The engineering was accomplished using PCR and oligonucleotides entered herein as SEQ ID NO:3 and SEQ ID NO:4.

The oligonucleotide of SEQ ID NO:3 covered a unique NcoI site in the center of the RIPΔNIC gene and was used for cloning in a subsequent step. SEQ ID NO:3 also resulted in a modified sequence which encoded unique NotI and PstI sites. A second oligonucleotide (SEQ ID NO:4) was positioned at the 3' end of the gene outside the coding region and resulted in creation a unique EcoRI site. Following amplification, the resulting fragment encoding the 3' half of the RIP gene was cut with NcoI and EcoRI and used to replace the analogous fragment in RIPΔNIC. The resulting DNA had the sequence entered herein as SEQ ID NO:5 and was designated RIP-1. RIP-1 had the amino acid sequence entered herein as SEQ ID NO:6.

RIP-2 was constructed as follows using RIP-1. Two oligonucleotides which were complimentary to each other, entered herein as SEQ ID NO:7 and SEQ ID NO:8, were prepared having sticky ends at the 5' and 3' ends corresponding to NotI and PstI sites, respectively. When added together, the two oligonucleotides joined to became double stranded. The double stranded oligonucleotide encoded an amino acid sequence wherein all of the charged amino acids were changed to lysine. The modifications included changing both positively (arginine) and negatively charged (aspartic and glutamic acids) residues to lysine. The resulting nucleic acid fragment was named RIP-2 and had the DNA and amino acid sequence disclosed herein as SEQ ID NO:9 and SEQ ID NO:10, respectively.

A plasmid containing DNA according to SEQ ID NO:9 was expressed in *E. coli* strain, BL21(DE3) using the T7 expression system using the expression conditions as previously described by Hey et al., (1995), Plant Physiol. 107:1323–1332). Lysates prepared from the cells containing the RIP-2 gene behind a T7 promoter produced full length RIP-2 polypeptide and was visualized by both Coomassie blue staining and Western blot as a protein having a molecular size of ca. 31 kDa.

RIP-3 was constructed from RIP-2 as follows. An NcoI site just upstream of the lysine enriched insertion in RIP-2 (SEQ ID NO:9) was eliminated by changing the DNA base C at position 433 to DNA base G thus facilitating further engineering. The modification was made by digesting the DNA having the sequence according to SEQ ID NO:9 with KpnI and NcoI and replacing said KpnI I to Nco I fragment of RIP-2 with the double stranded oligonucleotide disclosed herein as SEQ ID NO:11 and SEQ ID NO:12. This change resulted in elimination of the NcoI site thus producing a DNA fragment having the sequence entered herein as SEQ ID NO:13. This also resulted in a protein having the amino acid sequence entered herein as SEQ ID NO:14, being similar to the amino acid sequence according to SEQ ID NO:10 except having an amino acid change of threonine to serine at amino acid position 128. The resulting gene was designated RIP-3.

The 3' end of the RIP-3 gene (SEQ ID NO:13) was modified in a several step procedure. The first step required that several acidic and polar residues at the carboxy terminus be replaced with lysine. In addition, two restriction sites, SphI and XhoI, were added to facilitate addition of a PMC sub-domain by which the protein could be either recognized by antisera against said sub-domain or so that the protein could be more easily purified using affinity matrix columns. The changes were introduced by amplifying RIP-3 with oligonucleotides entered herein as SEQ ID NO:11 and SEQ ID NO:15. Amplification of RIP-3 with these primers resulted in a 530 bp product which was subcloned into pBCKS+ (Stratagene, La Jolla Calif.) and characterized with restriction enzymes to ensure it represented the modified 3' half of the RIP gene (SEQ ID NO:38). This plasmid was designated pBC:3'.

RIP-4 was constructed from RIP-3 by introduction of the modified 3' half of the RIP gene (SEQ ID NO:36) into RIP-3. This required cutting of the DNA entered previously as SEQ ID NO:36 with SphI followed by treatment with T4 DNA polymerase to create a blunt end and eliminate the site. The plasmid was then cut with PstI creating two fragments in the mixture, each having one PstI end and one blunt end. The vector fragment (containing the origin of replication) carried the Ampicillin resistance gene. The plasmid pBC:3', was cut with BamHI and also treated with T4 DNA polymerase to create a blunt end followed by cutting with PstI to create the following: a mixture of two fragments, a vector fragment (containing the chloramphenicol resistance gene) and the insert fragment containing the modified 3' end of pBC:3'. Both fragments had, as above, one PstI end and one blunt end. The two cut plasmid samples were mixed and ligated. Recombinants were identified by selection first on Ampicillin followed by restriction analysis. Expression of the RIP-3 clones in *E. coli* confirmed that the clones produce RIP-4 polypeptide (~32 kDa), which was slightly larger than that produced by the parent clone. The DNA and protein sequences of RIP-4 are therefore entered herein as SEQ ID NO:16 and SEQ ID NO:17, respectively.

The gene encoding RIP-5 was created from RIP-4 as follows herein. A PMC sub-domain was used and fused to the RIP-4 coding sequence. The sub-domain was amplified from a plasmid containing the PMC gene (SEQ ID NO:37) using the oligonucleotides entered herein as SEQ ID NO:18 and SEQ ID NO:19. The primers bracketed the entire cystatin domain coding sequence and additionally engineer in a 5' SphI site and a 3' XhoI site. The amplified 335 bp fragment having a DNA and amino acid sequence according to SEQ ID NO:20 and SEQ ID NO:21, respectively, was cloned into the SmaI site of plasmid pBCKS+ (Stratagene, La Jolla, Calif.) and shown to contain both engineered SphI and XhoI sites by restriction analysis. A single clone was selected and cut with SphI and XhoI. The resulting 335 bp fragment was purified by agarose gel electrophoresis and ligated into the SphI and XhoI sites of RIP-4. Those clones shown to contain the PMC gene segment were identified and characterized. The new recombinant gene, designated as RIP-5, had a DNA and amino acid sequence according to SEQ ID NO:22 and SEQ ID NO:23, respectively.

KRIP was constructed from RIP-5 as follows herein. The final modification of the 5' end was made in a single step by amplifying RIP-5 with oligonucleotides entered herein as SEQ ID NO:24 and SEQ ID NO:19. The entire gene, having a DNA and amino acid sequence according to SEQ ID NO:25 and SEQ ID NO:26, respectively, was amplified and subcloned into pBCKS+ cut with SmaI. Recombinants were selected on chloramphenicol, screened for blue/white selection using XGAL [5-bromo-4-chloro-3-indolyl-β-D-galactoside], confirmed with restriction analysis, and sequenced as described previously. KRIP polypeptide differed substantially from RIPΔNIC both in molecular weight (~45 kDa vs. ~28 kDa) and lysine composition (~14.4 mole percent vs. ~9.4 mole percent).

EXAMPLE 3

Cloning of the Gene Encoding 10 kDa Rice Prolamin (RP-10) Gene with and Without the Signal Peptide The gene encoding the 10 kDa rice prolamin protein (hereinafter RP-10) coding region including the signal peptide (Masumura et al., (1989) Plant Molecular Biology 12:123–130; Feng et al., (1990) Nucleic Acid Research, 18:683) was cloned from rice genomic DNA using PCR methods. Rice genomic DNA was extracted as described by Dellaporta et al., (1985) Molecular Biology of Plants: A Laboratory Course Manual. Cold Spring Harbor Laboratory, Cold Spring Harbor, N.Y.). A 5' primer (SEQ ID NO:27) was used to introduce a NcoI site at the translation initiation codon. The 3' primer (SEQ ID NO:28) encoded a SstI site 7 bp downstream of the translation stop codon. A Perkin Elmer Cetus Thermocycler (Norwalk, Conn.) was used for this and all subsequent PCR amplifications using the conditions recommended by the manufacturer. Gene amplification parameters were as follows: 35 cycles of [96° C. for 1 min; 55° C. for 2 min; and 72° C. for 3 min]. Total reaction volume was 100 μL, containing ca. 500 ng of template DNA and 50 pmol of each primer (SEQ ID NO:27 and SEQ ID NO:28). These primers were used to PCR amplify a 418 bp fragment having the sequence entered herein as SEQ ID NO:29. The PCR fragment was then gel purified and blunt-end ligated into the cloning vector pBC as described herein.

Further modifications to the RP-10 coding region were made to eliminate 2 internal NcoI sites (positions 107–112 and positions 116–121 in SEQ ID NO:29) which would interfere with subsequent cloning steps. The internal sites were removed by digesting the PCR amplified DNA fragment (SEQ ID NO:29) with BglII/BamHI to remove a 126 bp fragment. This fragment was then replaced with a BglII/BamHI fragment having a modified DNA sequence yet encoding for the identical amino acid sequence as the previously removed fragment. The sequence modification, the changing of base 108 and 117 of SEQ ID NO:29 from a C to T, was made by making an oligonucleotide wherein the DNA base pairs were changed to the desired sequence. Using this crude DNA synthesis mixture as template, the correct replacement fragment was PCR amplified using the oligonucleotides entered herein as SEQ ID NO:39 and SEQ ID NO:40. The amplified fragment was gel purified, restricted with BglII and BamHI, and cloned into the previously digested RP-10 coding region thereby creating the DNA sequence entered herein as SEQ ID NO:30. The amino acid sequence of the protein encoded therein is entered herein as SEQ ID NO:31. The RP-10 gene was then released as an NcoI/SstI fragment and ligated in plasmid pDAB356 to create pDAB1701 as described herein.

The nucleic acid fragment described above (SEQ ID NO:30) was cloned into the plasmid pET-9d (Novagen, Madison, Wis.). Following ligation, this material was then restricted with NcoI and BamHI thereby removing a 126 bp fragment. Oligonucleotides, entered herein as SEQ ID NO:32 and SEQ ID NO:33, were synthesized as described herein having NcoI and BamHI ends compatible to the NcoI/BamHI fragment previously removed. Bacteriophage T4 Polynucleotide kinase was used to phosphorylate the ends of the DNA strands which were then annealed as described previously (Sambrook et al., (1989) Molecular Cloning, a Laboratory Manual, $2^{nd}$ edition. Cold Spring Harbor Laboratory Press). This annealed oligomer was then ligated into the previously digested NcoI and BamHI sites of the pET-9d construct containing the DNA according to SEQ ID NO:30. This resulted in removal of RP-10 signal peptide sequences, maintenance of the correct reading frame, and creation a gene according to SEQ ID NO:34 encoding for the protein having the amino acid sequence according to SEQ ID NO:35. This plasmid was named pET-9dSP-.

EXAMPLE 4

Expression of the Plasmid pET-9dSP- in *E. coli*

Heterologous expression of RP-10 using plasmid pET-9dSP- in *E. coli* was performed as described herein with slight modifications. The *E. coli* strain BL21(DE3) (Novagen, Madison, Wis.) was utilized for all expression experiments. Following transformation with plasmid pET-9dSP- and selection of the *E. coli* on a Luria broth agar transformation plate containing 25 μg/mL Kanamycin), expression cultures were initiated by scraping ¼ of the confluent cell growth into 2 mL of Luria Broth (LB) with 25 μg/mL Kanamycin. They were grown 20 to 30 min at 37° C. on a rotating wheel, then induced with 5 mM IPTG (isopropylthio-β-galactoside) and grown at 37° C. for 5 to 6 hr. The cells were pelleted at 1000×g for 10 min, washed one time with TES [10 mM Tris pH 8.0, 1 mM EDTA, 100 mM NaCl], repelleted and frozen at −70° C.

The protein of interest was extracted on ice from the expression lysates by complete sonication (Soniprep 150, (Curtin Matheson Scientific Inc. Florence Ky.) High setting) in either urea extraction buffer [62.5 mM Tris-HCl pH 8.0, 1 mM EDTA, 4 M urea, 2% (v/v) 2-mercaptoethanol (β-ME), 200 μg/mL Phenylmethylsulfonyl fluoride (PMSF)] or alcohol extraction buffer [60% (v/v) N-propanol, 2% (v/v) 2-mercaptoethanol, and 200 μg/mL PMSF]. Following complete sonication, lysates were centrifuged at 4° C. for 10 min at 4000×g. Supernatants and pellets were then analyzed by gel electrophoresis on a Phastgel System using High Density gels with SDS buffer strips (Pharmacia, Piscataway, N.J.). A 10 kD protein was observed in the pellet fraction of the Urea method and the N-propanol supernatant fraction.

The *E. coli* expression experiment was subsequently scaled up to prepare sufficient RP-10 protein to provide enough antigen for polyclonal antibody production. The plasmid pET-9dSP- (2 μg) was transformed into BL21 cells and the cells were plated at 100 μL per plate (LB agar with 25 μg/mL Kanamycin). Plated cells were grown overnight and then scraped into 50 mL of LB containing 25 μg/mL Kanamycin. Cell masses were thoroughly dispersed by refluxing with a transfer pipette. The cell suspension was then transferred to 200 mL of LB with 25 μg/mL Kanamycin in a 1 L flask. Cultures were placed in a shaker having a speed of 250 rpm at 37° C. After growing for 0.5 hr, cells were induced with 5 mM IPTG and allowed to incubate for an additional 5 hr at 37° C. Cells were then collected by centrifugation at 1000×g for 10 min. Following, the pelleted cells were washed one time with TES [10 mM Tris pH 8.0, 1 mM EDTA, 100 mM NaCl] and frozen at −70° C. until extraction.

Proteins were purified for antibody production as follows. The expressed RP-10 was solubilized as described above using the n-propanol buffer. The supernatant from that extraction was then lyophilized to dryness and electrophoresed on a sodium dodecyl sulfate polyacrylamide gel electrophoresis (SDS-PAGE) gel as described herein. To some gels, the protein was stained with 0.2% (w/v) Coomassie blue for visualization. The band of interest was then excised and the protein was sent for antibody production in the gel matrix. Rabbit polyclonal antibody production against RP-10 was performed as a service by The Berkley Antibody Co., Richmond, Calif. To other gels, the proteins therein were electroblotted to polyvinylidene difluoride (PVDF) paper following the method of Towbin et al., (1979) Proc. Natl. Acad. Sci. USA 76, 4350–4354 and amino-terminal sequenced by the Harvard Microchemistry Facility, Cambridge, Mass. Amino terminal sequencing revealed that the protein of interest had the expected sequence.

EXAMPLE 5

The Design of the Plant Transformation Vector pDAB1701

The plasmid pDAB1701, a 4852 bp plant transformation plasmid similar to pDAB356, contained the γ-zein promoter, RP-10 gene, and a nopaline synthase (hereinafter Nos) polyadenylation sequence. It was comprised of the following: in plasmid pDAB1701 nucleotides 1–404 from pUC 18 which include lac operon sequence from base 238 to base 404 and ends with the HindIII site of the M13mp18 polylinker (Norrander et. al. (1983) Gene 26:101–106), nucleotides 405–411 of pDAB1701 correspond to a linker nucleotides 412–668 correspond to the Nos polyadenylation sequence (DePicker et. al., (1982) J. Molec. Appl. Genet. 1:561–573); nucleotides 669–690 correspond to a linker, nucleotides 691–1095 correspond the RP-10 coding region described by SEQ ID NO:30, nucleotides 1096–1108 correspond to a DNA linker, nucleotides 1109–2596 correspond to nucleotides 1078 to 2565 of the published maize γ-zein sequence (Das et. al., (1991) Nucleic Acids Research 19:3325–3330). The γ-zein sequence was modified to contain a 5' Kpn I site and 3' BamHI/SalI/Nco I sites. Nucleotides 2597–2615 of pDAB1701 correspond to a DNA linker, nucleotides 2616–4852 correspond to bases 450 to 2686 of the published pUC 18 sequence (Norrander et. al. (1983) Gene 26:101–106).

EXAMPLE 6

Method for Transformation of Embryogenic Type II Callus

Plasmids containing gene constructs were tested for expression in transgenic maize plants. The transgenic plants were initiated in embryogenic Type II callus tissue. Type II callus cultures were initiated from immature zygotic embryos of the genotype "Hi-II." (Armstrong et al, (1991) Maize Cooperation Newsletter, pp.92–93). Embryos were isolated from greenhouse-grown ears from crosses between Hi-II parent A and Hi-II parent B or F2 embryos derived from a self- or sib-pollination of a Hi-II plant. Immature embryos (1.5 to 3.5 mm) were cultured on initiation medium consisting of N6 salts and vitamins (Chu et al, (1978) The N6 medium and its application to anther culture of cereal crops. Proc. Symp. Plant Tissue Culture, Peking Press, 43–56) 1.0 mg/L 2,4-dichlorophenoxyacetic acid (2,4-D), 25 mM L-proline, 100 mg/L casein hydrolysate, 10 mg/L $AgNO_3$, 2.5 g/L GELRITE, and 20 g/L sucrose, with a pH of 5.8. Selection for Type II callus took place for ca. 2–12 weeks. After four weeks callus was subcultured onto maintenance medium (initiation medium in which $AgNO_3$ was omitted and L-proline was reduced to 6 mM).

For blasting 70 μg of plasmid DNA was precipitated onto 60 mg of alcohol-rinsed, spherical gold particles 1.0 μm in diameter (Aldrich Chemical Co., Milwaukee, Wis.) per construct. Precipitation was accomplished by adding 74 μL of 2.5 M $CaCl_2$ and 30 μL of 0.1 M spermidine (free base) to 300 μL of plasmid DNA. The solution was immediately vortexed and the DNA-coated gold particles were allowed to settle. The resulting clear supernatant was then removed and the gold particles were resuspended in 1 mL of absolute ethanol. This suspension was diluted with absolute ethanol to obtain 15 mg DNA-coated gold/mL.

Helium blasting accelerated suspended DNA-coated gold particles towards and into the prepared tissue targets. The device used was an earlier prototype of that described in U.S. Pat. No. 5,141,131 which is incorporated herein by reference. Tissues were covered with a stainless steel screen (230 μm openings) and placed under a partial vacuum of 25 inches of Hg in the device chamber. The DNA-coated gold particles were further diluted 1:1 with absolute ethanol prior to blasting and were accelerated at the embryo target once using a helium pressure of 1500 psi, with each blast delivering 20 μL of the DNA/gold suspension.

For the production of transgenic corn plants, embryogenic Type II callus cultures were prepared and used. In so doing, ca. 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4–16 h pre-treatment, tissue was transferred to culture dishes containing blasting medium (osmotic media solidified with 20 g/L tissue culture agar (JRH Biosciences, Lenexa, Kans.) instead of 7 g/L GELRITE (Schweizerhall). Helium blasting was performed as described herein. Immediately post-blasting, the tissue was transferred to osmotic media for a 16–24 h recovery period. Afterwards, the tissue was divided into small pieces and transferred to selection medium (maintenance medium lacking casein hydrolysate and L-proline but having 30 mg/L BASTA (Agrevo)). Every four weeks for 3 months, tissue pieces were non-selectively transferred to fresh selection medium. After 6 weeks and up to 20 weeks, callus sectors found proliferating against a background of growth-inhibited tissue were removed and isolated. The resulting BASTA-resistant tissue was subcultured biweekly onto fresh selection medium.

Plant regeneration was initiated by transferring callus tissue to cytokinin-based induction medium, which consisted of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA, and 2.5 g/L GELRITE (Schweizerhall) at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tubes containing SH medium (SH salts and vitamins (Schenk and Hildebrandt, (1972) Can. J. Bot. 50:199–204), 10 g/L sucrose, 100 mg/L myo-inositol, 5 mL/L FeEDTA, and 2.5 g/L GELRITE (Schweizerhall), pH 5.8). Plantlets were transferred to 10 cm pots containing approximately 0.1 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). Temperatures were generally maintained at 22° C. and 27° C. during the night and day periods, respectively. At the 3–5 leaf stage, plants were transferred to five gallon pots containing approximately 4 kg METRO-MIX 360.

Primary regenerants ($R_1$ plants) were cross-pollinated when possible after an additional 6–10 weeks in five gallon pots to the elite line CQ 806 (Mycogen Seeds, San Diego, Calif.). Southern analysis, as described herein, was used to select those plants containing the transgene of interest. Typically, $R_1$ seed were collected at 40–45 days post-pollination.

EXAMPLE 7

Southern Analysis of Transformed Callus and Plant Tissues

BASTA resistant lines transformed with various plasmids were characterized by Southern analysis to confirm the presence of the transgene using a DNA probe specific for the coding region of the gene of interest. DNA from both callus and leaf material was analyzed.

For callus, the material was soaked in distilled water for 30 min. and transferred to a new petri dish prior to lyopholization. Leaf material from plants was harvested at the 6–8 leaf stage. Genomic DNA was prepared from lyophilized tissue as described by Saghai-Maroof et. al. ((1984) Proceed. Nat. Acad. Sci. USA 81:8014–8018). Eight μg of each DNA was digested with the restriction enzyme(s) specific for each plasmid construct using conditions suggested by the manufacturer (Bethesda Research Laboratory) and separated by electrophoresis on a 0.8% agarose gel. The DNA was then blotted onto nylon membranes as described by Southern ((1975) J. Mol. Biol., 98:503–517). The radioactive probe was then hybridized to the genomic DNA on the blots in 45 mL of minimal hybridization buffer [10% polyethylene glycol, 7% sodium dodecyl sulfate, 0.6×SSC, 10 mM sodium phosphate, 5 mM EDTA and 100 μg/mL denatured salmon sperm DNA] overnight at 60° C. After hybridization, blots were washed at 60° C. in 0.25×SSC and 0.2% SDS for 45 min., blotted dry and exposed to XAR-5 film (Kodak) overnight on two intensifying screens (DuPont).

EXAMPLE 8

Immunoblot Analysis of RP-10 Protein in Transgenic Seed

Proteins from kernels of CQ806, a southern negative RP-10 R1 transgenic line, and a southern positive RP-10 R1 transgenic line containing the RP-10 gene from plasmid pDAB1701 as described herein were tested for the presence of transgenically expressed RP-10. Pools of forty kernels from each of the R1 plants were ground to flour in an electric coffee grinder. One hundred mg of said flour was then extracted mechanically in 1 mL of an alcohol-based extraction buffer [60% (v/v) n-propanol, 2% beta-mercaptoethanol, 200 µg/mL PMSF]. Extracts were then centrifuged for 10 min at 4° C. Supernatants were transferred to fresh Eppendorf tubes on ice. Protein was quantitated using the BioRad Protein Assay Kit (BioRad, Hercules, Calif.). Following quantitation, 10 µg of total protein was separated using SDS-PAGE on 17–27% gradient gels (Integrated Separation Systems, Natick, Mass.). One µg of E. coli lysate containing expressed RP-10 protein was included as a positive control. Following electrophoresis, the proteins were electroblotted (Pharmacia Semi-Dry Electroblotter; Pharmacia, Piscataway, N.J.) to ECL-Hybond membrane (Amersham, Arlington Hts., Ill.). Included on the blot was 1 µg of E. coli lysate containing expressed RP-10 protein. The nonspecific binding sites of the blots were blocked with 10% dry milk in TBS [20 mM Tris-HCl pH 7.5, 150 mM NaCl, and 0.05% Tween 20] for 1 hr. After blocking, blots were reacted with polyclonal antisera generated against the E. coli expressed RP-10 protein as described herein. Secondary antibody was goat anti-rabbit conjugated to horseradish peroxidase (BioRad, Hercules, Calif.). Immunoreactive proteins were detected using the ECL Western Blotting Detection Reagents (Amersham, Arlington Hts., Ill.)). Extraction and analysis of individual maize kernels were performed in the same manner.

Analysis of pooled seed from transgenic plants known to contain the RP-10 gene, as determined by Southern analysis as described herein, produced a Western signal having the same molecular weight as the E. coli produced protein. No Western signal corresponding to a protein having that molecular weight was detected for either CQ806 (negative non-transformed plants) or transformed plants not having the gene of interest (negative transformed plants).

Immunoblot analysis of individual kernels from several different RP-10 southern positive lines demonstrated the presence of RP-10 protein. Transgenic events in which detection of an immunoreactive product was observed correlated directly with positive Southern analysis data.

EXAMPLE 9

Construction of Plasmids pDAB358, pDAB364, and pDAB308

The Potato Multicystatin (hereinafter PMC) gene encodes a multidomain cysteine protease inhibitor protein. A genomic clone of the PMC gene (Waldron et al., (1993) Plant Molecular Biology, 23:801–812) having the sequence as entered herein as SEQ ID NO:37 was cloned behind the γ-zein promoter to create plasmid pDAB358.

The plasmid pDAB358 is a 7940 base pair plasmid derived from pUC19. Nucleotide #1 falls between the unique Nde I and Ssp I sites of pUC19. The following plasmid description begins with nucleotide #1 and continues toward the β-lactamase coding region which is read in the 5' to 3' orientation proceeding in a clockwise direction. Bases 1–2231 correspond to bases 1–2231 of puc19 (Messing, J. (1983) in "Methods in Enzymology" (Wu, R. et al., eds.) 101:20–78. Bases 2232–2261 correspond to a polylinker comprised of the restriction sites EcoRI, XhoI and KpnI. Bases 2262–3744 correspond to bases 1078–2565 of the 5' flanking region of the γ-zein gene, GenBank Accession #X58197 (Das, et al., (1991) Nucleic Acids Research, 19:3325–3330). The γ-zein sequence includes the following changes relative to the published sequence: a T deletion at base 1175; TACA deletion at bases 1683–1686; a C to T substitution at nucleotide 1888; an A deletion at base 2241; an A insertion at base 2428. Bases 3745–3757 of plasmid pDAB358 includes a BamHI site, a SalI site, and the first two bases of an NcoI site. Bases 3758–7255 correspond to the PMC genomic clone, bases 671–4168, GenBank accession #L16450 (Waldron et al., (1993) Plant Molecular Biology, 23:801–812). Bases 7273–7529 correspond to bases 1298–1554 of nopaline synthase (DePicker et al., (1982) J. Molec. Appl. Genet. 1:561–573). In conclusion, bases 7545–7940 correspond to bases 2291–2686 of puc19.

The plasmid pDAB364 (5647 bp) is essentially pDAB358 with the following exceptions. The polylinker from nucleotides 2232 to 2249 consists of the following restriction sites, EcoRI, SacI and KpnI. Nucleotides 3746–4951 immediately following the γ-zein promoter correspond to the KRIP coding region according to SEQ ID NO:25.

Plasmid pDAB308 is a 4496 base pair plasmid having the following: position 1 corresponds to base 441 of pUC19 (Messing, J. (1983) in "Methods in Enzymology" (Wu, R. et al., Eds.) 101:20–78) and is the base after the final C residue of the SphI site. Reading on the strand contiguous to the LacZ gene coding strand, which corresponds to nucleotides 4468 to 4496 and 1851 to 2105 of plasmid of pDAB308. Nucleotides 20 to 271 of plasmid pDAB308 correspond 7093 to 7344 of the Cauliflower Mosaic Virus CabbS strain, hereinafter CaMV, (Franck, et al., (1980) Cell 21:285–294); nucleotides 272 to 279 of plasmid pDAB308 correspond to CATCGATG; nucleotides 280 to 626 of plasmid pDAB308 correspond to nucleotides 7093 to 7439 of CaMV; nucleotides 647 to 666 of plasmid pDAB308 correspond to nucleotides 167 to 186 of Maize Streak Virus, hereinafter MSV, (Mullineaux, et al., (1984) EMBO J. 3:3063–3068); nucleotides 667 to 756 of plasmid pDAB308 correspond to nucleotides 188 to 277 of MSV; nucleotides 757 to 849 of plasmid pDAB308 correspond to bases CA followed by nucleotides 120 to 210 of maize alcohol dehydrogenase 1S, hereinafter Adh1, (Dennis, et al., (1984) Nucl. Acids Res. 12:3983–4000) containing parts of exon 1 and intron 1; nucleotides 850 to 967 of plasmid pDAB308 correspond to nucleotides 555 to 672 of Adh1 containing parts of intron 1 and exon 2; nucleotides 978 to 1017 of plasmid pDAB308 correspond to nucleotides 278 to 317 of MSV; nucleotides 1018 to 1566 of plasmid pDAB308 correspond to a modified BAR coding region from pIJ4104 (White et al., (1990) Nucl. Acids. Res. 18:1062) having the AGC (serine) codon in the second position replaced by GCC (alanine) and nucleotide 546 changed from G to A; nucleotides 1591 to 1847 of plasmid pDAB308 correspond to nucleotides 1298 to 1554 of nopaline synthase (DePicker, et al., (1982) J. Molec. Appl. Genet. 1:561–573); and nucleotides 1848 to 4496 of plasmid pDAB308 correspond to the base G followed by the rest of pUC 19.

EXAMPLE 10

Production of Gentically Uniform Lines From Transformation Events Involving pDAB308/ pDAB358: Evaluation for Protein, Amino Acid Content and Measurement of PMC Accumulation by Western Analysis Primary regenerates (R0 plants) cobombarded with plasmids pDAB308 and pDAB358 were utilized as the seed parent in crosses with the inbred line CQ806. Test-cross progeny (R1) produced by these pollinations were obtained and these seed were planted in the greenhouse for self-pollination. Self-pollinations resulted in seed and these self pollinated (R2) progeny were planted in the greenhouse. Southern analysis was performed on all R2 plants confirming the presence or absence of the transgene. Some of these plants were then self-pollinated resulting in seed production. Seed were produced that resulted from pollination (sib matings) by plants from the same line of descent or the same transformation event. Additional plants produced seed from pollination with the inbred line CQ806.

Since each transformation event carried a single copy of the bar gene conferring resistance to the herbicide BASTA, the genetic state of the introduced DNA could be determined by the pattern herbicide resistance. The seed from different lines were planted in separate 4 inch pots in the greenhouse, where they were allowed to germinate and develop to the 3–4 leaf stage. All plants at this stage of development were treated with a 2% Basta aqueous solution. Survival was scored after 72 hr.

Seed lines were classified into 3 categories: homozygous lacking the gene; segregating; and uniformly expressing the gene. Among the class that was uniformly expressing the gene the seed lines could be further subdivided into those which were homozygous, resulting form self-pollination, and those which were uniformly hemizygous, resulting from a cross to the inbred line CQ806 or sib pollination with a homozygote. Seed from lines which uniformly expressed the gene and lines which lacked the gene were sent to Ralston Analytical Laboratories (Ralston Purina Company, Checkerboard Square, St. Louis, Mo. 63164). Each sample was tested for protein content and acid stable amino acid content. The moisture content of each sample was measured on a ground sample using an analytic moisture content balance.

Protein content measurements, described in detail in Official Methods of Analysis of the Association of Official Analytical Chemist, P. A. Cunniff, Ed., 16$^{th}$ Edition. (1995); Method 990.03, Locator #4.2.08; AOAC International, Gaithersburg, Md., involved grinding the sample to a fine powder. The powder was mixed with oxidizing agents and a catalyst in a combustion tube. The tube was heated, oxidizing the sample to free nitrogen oxides which were catalyzed to elemental nitrogen gas. The nitrogen gas was carried into a thermal conductivity detector with helium gas. Nitrogen content was then converted to percent protein by multiplying by 6.25%.

Amino acid analysis, performed as described in Official Methods of Analysis of the Association of Official Analytical Chemist, P. A. Cunniff, Ed., 16$^{th}$ Edition. (1995); Method 990.03, Locator #4.2.08; AOAC International, Gaithersburg, Md., involved mixing the proteins with a hydrochloric acid solution in a modified Kjeldahl flask. To prevent oxidation of the amino acids, as much oxygen as possible was removed from the flask by repeated heating and freezing, under vacuum. The neck of the flask was heat sealed, and the flask heated in a 110° C. oven for 20 hours. Protein in the sample was hydrolyzed to amino acids by the hot hydrochloric acid solution. The samples were cooled, opened, mixed with internal standard and adjusted to pH 2.2. The amino acids were then separated on an ion exchange column by a pH gradient elution in an amino acid analyzer with controlled column temperatures. The separated amino acids were subsequently reacted with ninhydrin, forming color complex solutions that were measured spectrophotometrically. The concentration of each amino acid was quantitated against a standard solution of amino acids of known concentration and internal standard.

TABLE 5

Grain moisture, total protein and lysine contents of transgenic and controls lines from 308/358 transformation events. Expressed as gm/100 gm dry weight.

| Line | Grain Moisture | Total Protein | Lysine Content |
|---|---|---|---|
| 308/358 Self[a] | 11.97 | 17.72 | 0.40 |
| 308/358 × CQ806[b] | 11.50 | 16.95 | 0.37 |
| Transgenic Mean | 11.73 | 17.33 | 0.38 |
| Control Mean | 12.13 | 15.47 | 0.35 |
| Transgenic Mean − Control Mean | −0.40 | 1.86 | 0.03 |
| Percentage Change | −3.3% | 12.02% | 8.7% |

[a]Homozygous;
[b]Uniformly hemizygous; moisture, protein and lysine expressed as g/100 g dry weight As shown in Table 5, homozygous and uniformly hemizygous lines expressing the PMC gene were analyzed for protein content. The kernels produced from transgenics plants expressing PMC had slightly lower grain moisture contents, higher total protein, and higher lysine content.

The expression levels of PMC were quantitated (Table 6) as follows. A sample was taken from each transgenic line expressing PMC. Each sample was then ground to a fine powder using a small coffee grinder. A 200 mg sample was weighed into a 1.5 ml Eppendorf tube and 800 μL of extraction buffer [GUS Plant Lysis buffer (Tropix, Inc. Bedford, Mass.) having 1% polyvinylpyrolidone, 50 mg/mL antipain, 50 mg/mL leupeptin, 0.1 mM chymostatin, 5 mg/ml pepstatin and 0.24 mg/ml Pefabloc™ (Boehringer Mannheim, Indianapolis, Ind.)] was added. The samples were placed on ice for 5–10 min, a small amount of silica sand was added and the samples were ground 3 separate times (10–15 sec). Samples were placed back on ice between grindings. After a final incubation on ice for at least 10 min, the samples were centrifuged at 16,000×g for 5 min. Supernatants were recovered and centrifuged a second time as described above. The supernatants were recovered, frozen on dry ice, and stored at −70° C. until further use. Protein concentrations were measured using the Bradford method with a kit produced by Sigma Diagnostics (St. Louis, Mo.) according to instructions.

Because of the high expression level of the PMC protein in these transgenic lines, only 1 μg of protein was loaded per sample on the gel. Protein standards consisted of 20, 5, 1.25, 0.3 and 0 ng of purified PMC loaded in 1 μg of protein extracted from the inbred line CQ806. The polyacrylamide gels utilized were precast 4–20% Miniplus SepraGels™ (Integrated Separation Systems, Natick, Mass.). Prior to loading, the samples and standards were heated for 3 min at 90° C. Each gel was run at 50 mA at a constant voltage until the bromophenol blue dye was 0.5 cm from the end of the gel. The buffer utilized was Seprabuff™ (Integrated Separation Systems, Natick, Mass.). The separated proteins were transferred to Hybond™ECL™ nitrocellulose membrane (Amersham Life Sciences, Arlington Hts., Ill.) using the electroblot procedure described herein. The electroblot buffer [25 mM Tris, 192 mM glycine, 20% methanol adjusted to pH 8.2] was maintained at 4° C. throughout the 2 hr transfer procedure. The transfer voltage was 100 v. After the transfer was complete, the membrane was transferred to 50 mL of TBST [20 mM Tris, 137 mM NaCl, 0.1% Tween 20, pH7.6)+5% dry milk]. The membranes were gently agitated in the TBST+milk for 16 hr at 4° C. After 16 hr, the membranes were removed from the TBST+milk and incubated in 50 mL fresh TBST+milk which included a 1:5000 dilution of the rabbit anti-PMC primary antisera. The membranes were agitated for 1 hr at 150 rpm. Following the incubation with primary antisera, the membranes were washed 4 times with fresh TBST, 3×5 min, and 1×15 min. The membranes were then incubated for 1 hr in fresh TBST+milk which included a 1:5000 dilution of goat anti-rabbit IgG antibody conjugated with horseradish peroxidase. The same series of washes as described above were performed. After these washes were complete the ECL™ reagents (Amersham Life Sciences) were prepared by mixing equal quantities of Reagent A and Reagent B. The membranes were removed from the TBST, drained briefly and then placed in approximately 20 mL of the reaction mixture for 1 min with agitation. The membranes were again drained briefly, wrapped in plastic wrap and placed in x-ray cassettes. A series of exposures were made ranging from 1 sec to 1 min. The film utilized was Hyperfilm™ECL™ (Amersham Life Sciences).

Quantitation was done using a Molecular Dynamics Personal Densitometer. Integrated volume was used for calculating protein concentrations, and peak height of the scans was analyzed to verify that the film was in the linear range of exposure. Analysis of the seed revealed several lines having transgenically produced PMC. The sizes of the immunologically reactive bands ranged from ca. 88 kDa to ca. 20 kDa. The individuals products were quantitated separately and the results were summed across all products to measure the overall expression level.

TABLE 6

Expression levels of γ-zein driven PMC in homozygous or uniformly hemizygous transgenic lines measured as a percentage of extractable protein.

| Line | Percent PMC Expression Level[a] |
|---|---|
| 308/358-19 × CQ806[b] | 0.36 |
| 308/358-17 Self[c] | 1.88 |
| 308/358-17.50 × 308/358-17.01[c] | 0.80 |

[a]Percentage of PMC protein relative to total extractable protein;
[b]Uniformly hemizygous PMC lines;
[c]Homozygous PMC lines

EXAMPLE 11

Western Analysis of 308/364 Transgenic Expressing Krip

Primary regenerates containing the pDAB364 gene (R0 plants) were recovered from independent transgenics events and pollinated with the inbred line CQ806. Seed from these plants were collected and samples were ground to a fine powder in a Braun model KSM2 coffee grinder. A 70 to 165 mg sample was placed in a 1.5 mL eppendorf tube and 140–400 µL protein extraction buffer as described herein was added to each tube. Samples were then processed as previously described. After a final incubation on ice for at least 10 min, samples were centrifuged at 16,000×g for 5 min, supernatants were recovered, and centrifuged a second time as described above. The supernatants were then recovered and frozen on dry ice and stored at −70° C. Protein contents were measured as described herein.

For Western analysis, 5 µg protein sample was loaded per lane on a SDS-PAGE gel. Protein standards consisted of 1 ng, 250 pg, 50 pg, and 0 pg of purified maize RIP loaded in 5 µg of protein extracted from the inbred line HO1 (Mycogen Seed, San Diego, Calif.). The polyacrylamide gels utilized were precast 12% gels (Integrated Separation Systems, Natick, Mass.). Prior to loading, the samples and standards were heated for 3 min at 90° C. Each gel was run at 50 mA at a constant voltage until the bromophenol blue dye was 0.5 cm from the end of the gel. The buffer utilized was Seprabuff™ (Integrated Separation Systems, Natick, Mass.). The separated proteins were transferred to Hybond™ECL™ nitrocellulose membrane (Amersham Life Sciences, Arlington Hts., Ill.) using the electroblot procedure described herein. Following completion of transfer, the membranes were and transferred to 50 mL of TBST as described herein. Western analysis was performed as described herein with the primary antibody was being a 1:2000 dilution of the rabbit anti-RIP primary antisera. min. A 1:5000 dilution of goat anti-rabbit IgG antibody conjugated with horseradish peroxidase was used as the secondary antibody. Detection of immunologically reactive proteins was accomplished using ECL™ reagents (Amersham Life Sciences, Arlington Ht., Ill.) as previously described.

Analysis of proteins within the seed from transgenic plants having the gene of interest revealed that these plants expressed many distinct protein products. Quantitation was performed by examining the presence of new protein products not found in the negative control lines. At least two distinct protein products were detected in transgenics that were completely lacking in controls. These products accumulated consistently across the 308/364 transformation events.

We claim:

1. A protein having the amino acid sequence of SEQ ID NO:2.

2. Corn seed containing the protein of claim 1.

3. Corn seed of claim 2 wherein said protein is produced by expression of nucleic acid comprising SEQ ID NO: 1.

* * * * *